US007842682B2

(12) United States Patent
Roncucci et al.

(10) Patent No.: US 7,842,682 B2
(45) Date of Patent: Nov. 30, 2010

(54) BORONATED METAL-PHTHALOCYANINES, PROCESS FOR THEIR PREPARATION, PHARMACEUTICAL COMPOSITIONS COMPRISING THEM AND USE THEREOF

(75) Inventors: Gabrio Roncucci, Colle Val D'elsa (IT); Giulio Jori, Padua (IT); Francesca Giuntini, Mercatale Val di Pesa (IT); Clara Fabris, Padua (IT); Giacomo Chiti, Montemurlo (IT); Moira Municchi, Pelago (IT); Donata Dei, San Gimignano (IT)

(73) Assignee: L. Molteni & C. Dei Fratelli Alitti, Scandicci (IT)

( * ) Notice: Subject to any disclaimer, the term of this patent is extended or adjusted under 35 U.S.C. 154(b) by 789 days.

(21) Appl. No.: 10/548,793

(22) PCT Filed: Mar. 11, 2004

(86) PCT No.: PCT/EP2004/002505

§ 371 (c)(1),
(2), (4) Date: Sep. 12, 2005

(87) PCT Pub. No.: WO2004/081014

PCT Pub. Date: Sep. 23, 2004

(65) Prior Publication Data

US 2006/0135478 A1   Jun. 22, 2006
US 2008/0009464 A9   Jan. 10, 2008

(30) Foreign Application Priority Data

Mar. 11, 2003   (IT)   .............................. FI2003A0063

(51) Int. Cl.
A01N 55/02   (2006.01)
A61K 31/555  (2006.01)
C07B 47/00   (2006.01)
C07D 487/22  (2006.01)

(52) U.S. Cl. .................................................... 514/185
(58) Field of Classification Search ................. 540/145; 514/185
See application file for complete search history.

(56) References Cited

U.S. PATENT DOCUMENTS 3,730,950 A   5/1973   Barnes et al.

FOREIGN PATENT DOCUMENTS

EP   0 906 758 A1   4/1999

OTHER PUBLICATIONS

Pinedo et al., "Translational Research . . . ", The Oncologist 2000; 5(suppl 1); 1-2.*
McMahon, G., "VEGF Receptor Signalin in Tumor Angiogenisis"., The Oncologist 2000; 5(suppl1); 3-10.*
Alam, F. et al., "Boron compounds for neutron capture therapy," XP002291250 retrieved from STN Database Accession No. 1990:455131; Database CHEMABS [Online] Chemicals Abstract Service, Columbus, Ohio US; 1990, Abstract.
Fabris, C. et al., "Photosynthesizing properties of a boronated phthalocyanine: studies at the molecular and cellular level," *Journal of Photochemistry and Photobiology B: Biology* 2001; 64(1):1-7.
Kahl, S. B. et al., "Synthesis and Characterization of a Boronated Metallophthalocyanine for Boron Neutron Capture Therapy," *Inorg. Chem.* 1996; 35:3878-3880.
Plater, M.J. et al., "Synthesis of soluble halogenated aryloxy substituted indium phthalocyanines," *J. Chem. Soc., Perkin Trans. I* 2002; 91-96.
Vladimir I. Bregadze et al., "Polyhedral boron derivatives of porphyrins and phthalocyanines," *Journal of Porphyrins and Phthalocyanines*, 2001; 5: 767-78.
John S. Sill et al., "Selective tumor kill of cerebral glioma by photodynamic therapy using a boronated porphyrin photosensitizer," *Proc. Natl. Acad. Sci. USA*, vol. 92, pp. 12126-12130, Dec. 1995.
R. Spryshkova et al., "Biodistribution Study of Novel Dodecaborate-Phthalocyanines in the B-16 Mouse Melanoma Model," *Frontiers in Neutron Capture Therapy*, edited by Hawthorne et al., Kluwer Academic, Plenum Publishers, New York 2001, pp. 1027-1032.
M. Graça H. Vicente, "Syntheses of carbon-carbon linked carboranylated porphyrins for boron neutron capture therapy of cancer," *Tetrahedron Letters*, 41: 7623-7627 (2000).
Friso, E. et al., "A novel $^{10}$B-enriched carboranyl-containing phthalocyanine as a radio- and photo-sensitising agent for boron neutron capture therapy and photodynamic therapy of tumours: in vitro and in vivo studies," *Photochem. Photobiol. Sci.* 2006; 5:39-50.
Mody, T., "Pharmaceutical development and medical applications of porphyrin-type macrocycles," *Journal of Porphyrins and Phthalocyanines* 2000; 4:362-367.

* cited by examiner

*Primary Examiner*—James O. Wilson
*Assistant Examiner*—Paul V. Ward
(74) *Attorney, Agent, or Firm*—Wolf, Greenfield & Sacks, P.C.

(57) ABSTRACT

The present invention relates to meta 1-phthalocyanines bearing at least a group containing boron isotopes $^{11}$B or $^{10}$B, covalently bound to the peripheral positions of meta 1-phthalocyanine nucleus; moreover it refers to the processes for their preparation, the pharmaceutical compositions comprising them and their use for the treatment of neoplastic and dysplastic pathologies.

10 Claims, 6 Drawing Sheets

BORONATED METAL-PHTHALOCYANINES, PROCESS FOR THEIR PREPARATION, PHARMACEUTICAL COMPOSITIONS COMPRISING THEM AND USE THEREOF

RELATED APPLICATIONS

This application is a national stage filing under 35 U.S.C. §371 of PCT International application PCT/EP2004/002505, filed Mar. 11, 2004, which was published under PCT Article 21(2) in English.

FIELD OF THE INVENTION

The present invention relates to metal-phthalocyanines bearing at least one group containing boron isotopes $^{11}$B or $^{10}$B covalently bound to the peripheral positions of the metal-phthalocyanine nucleus; moreover it refers to the processes for their preparation, the pharmaceutical compositions comprising them and their use for the treatment of neoplastic and dysplastic pathologies.

STATE OF THE ART

It is known that organic molecules, originating from the phthalocyanines macrocycle complexed with a diamagnetic metal and bearing proper substituents, once photo-activated by irradiation with light, are capable of generating reactive oxygen species (ROS).

Such compounds, developed for therapeutic purposes, have been recently widely described in the scientific literature and in the U.S. Pat. No. 5,965,598, in the European Patent Application No. 906 758 and in the European Patent No. 1 164 135, all in the name of the Applicant, where the use of these molecules in the photodynamic therapy of microbial infections, tumour and proliferative pathologies, as well as in the photodiagnosis and ex vivo sterilization procedures, is claimed, according to their distinctive selectivity for the above mentioned targets.

The derivatives described in the above cited patents and patent applications combine high quantum yields of singlet oxygen production, high absorptions in the red region of visible spectrum and optimum solubility in aqueous medium or formulations, suitable for topical administrations. The side chains, from one side provide the physical-chemical features required for the photosensitising efficiency, from the other guarantee the high bio-availability of the products, the fast metabolism of the derivatives and thus the final clearance for an optimal localization of the active molecules in the target, thus limiting their toxicity. It is also worth mentioning that the by-products, that may originate from the photobleaching process of the original derivatives after interaction with the light, are not toxic and could facilitate their clearance after the photodynamic treatment, the skin toxicity damage due to a potential delayed phototoxicity resulting limited.

Moreover, a therapy for the treatment of particularly aggressive neoplastic and displastic pathologies, known as Boron Neutron Capture Therapy (hereinafter called BNCT), has been recently described and is based on the administration of non-radioactive isotope $^{10}$B in conjunction with thermal neutrons. As reported in the state of the art, the interaction of (non-radioactive) $^{10}$B isotope with thermal neutrons generates high linear energy transfer particles such as $^4_2$He ($\alpha$ particles) and $^7_3$Li, causing cellular damage through ionization processes at subcellular level. Since those fission fragments have a mean free pathway which is approximately equivalent to the average diameter of mammalian cells, the success of BNCT therapy in the inactivation of tumour or hyperproliferative cells is dependent upon the possibility to achieve a sufficiently large endocellular concentration of boron atoms, that is a consequence of the localization of the carriers they are bound to, in neoplastic or dysplastic tissues.

$^{10}$B isotope derivatives bound to carriers having tumour targeting selectivity has been recently described (Stephan B. Kahl et al., *Inorg. Chem.* 1996, 35 3878-3880; M. G. Vicente et. al., *Tetrahedron Letters* 41 (2000) 7623-7627, Spryshkova R et al. *Frontiers in Neutron Capture Therapy* (2001) 1027-1032, Bregadze V. I. *Journal Porphyrin and Phthalocyanine* (2001) 5, 767-781); in these papers the effectiveness of phthalocyanines and porphyrins derivatives as regards BNCT treatment is demonstrated.

Moreover, in the article Fabris C. et al., *J. Photochem. Phobiol.* 64 (2001) 1-7 the synthesis of a mono-substituted zinc-phthalocyanine with a single boron cluster (undecahydro-closo-dodecaboromercaptocarbonylphenoxy) group is described, and it has been found that localization of this product is particularly efficient due to the optimal ratio between the phthalocyanine moiety and the substituent boron derivative. This compound showed remarkable biological characteristics and photodynamic efficiency, however the amount of boron carried to tumour cells proved to be less than the minimum dose of boron required for the BNCT treatment to be effective, which is 20 µg per g of tissue.

According to what has been previously discussed, there is a strong need for the availability of products having both photodynamic enhanced properties and specific cellular and subcellular uptake and bearing substituents with a sufficient number of boron atoms, in order to provide suitable boron concentration in tumor tissues or in areas affected by other pathologies characterised by cell hyperproliferation; such compounds will allow the sequential application of PDT and BNCT with all the advantages of selectivity and activity related to these treatments (Hill J. S. at al. *Proc. Natl. Acad. Sci. USA* 92 12126-12130). Toward this aim the preparation of the corresponding $^{11}$B-boronated derivatives is also of paramount importance, for the following reasons: 1) as $^{10}$B intermediates are quite expensive and hard to find, the synthetic procedures must be optimised on the products having the natural isotopic abundance; 2) many biological experiments, such as accumulation in tissues, permeability of biological barriers, metabolic pathway determination, etc, can be performed by using $^{11}$B-boronated derivatives in advance; 3) $^{11}$B containing phthalocyanines are themselves useful photosensitizers for PDT applications.

SUMMARY OF THE INVENTION

The Applicant has now surprisingly found that novel boronated metal-phthalocyanines, bearing up to eight peripheral substituents containing boron isotopes $^{10}$B, may be used as products for both BNCT and PDT. These products are able to carry amounts of boron greater than the minimum dose needed for the success of BNCT treatment into the tumour cells, while still showing a high photodynamic efficiency and a selective uptake in rapidly proliferating cells. This finding was unexpected on the light of the previously cited literature and know-how, where good uptake and localizing properties as well as optimal photodynamic characteristics were found for phthalocyanine derivatives having only one boron cluster substituent (undecahydro-closo-dodecaboromercaptocarbonylphenoxy).

Subject of the present invention are therefore compounds of general formula (I)

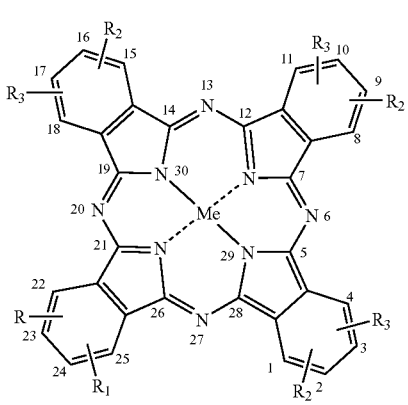

in which:

Me is chosen in the group consisting of Zn, AlOR$_4$ and Si(OR$_4$), wherein R$_4$ is chosen in the group consisting of H and C1-C15 alkyl, R, R$_1$, R$_2$ and R$_3$, equal or different from one other, are selected from H and groups (G)$_s$-(X)$_t$-(Y-Z)$_u$ wherein:

G is selected from the group consisting of O, S, SO, CH$_2$ and N;

X is selected from the group consisting of phenyl, linear or branched C1-C10 alkyl, C1-C10 alkenyl and C1-C10 alkinyl;

Y is selected from the group consisting of S, (CH$_2$)$_n$, phenyl, O—(CH$_2$)$_n$, (CH$_2$)$_n$—O—, (CH$_2$CH$_2$O)$_n$, CONH, NHCO, COO, COS, and, and 3-mercapto-pyrrolidine-2,5-dione;

Z is selected from the group consisting of $^{11}$B-(o,m,p-carborane), $^{11}$B-undecahydrododecaboromercaptyl, $^{11}$B-undecahydrododecaborate, $^{10}$B-(o,m,p-carborane), $^{10}$B-undecahydrododecaboromercaptyl and $^{10}$B-undecahydrododecaborate;

n is an integer comprised between 1 and 10;

s is 0, 1;

t is 0, 1;

U is an integer comprised between 1 and 3;

with the proviso that at least one among R, R$_1$, R$_2$ and R$_3$ is different from H. and when only one amongst R, R$_1$, R$_2$ and R$_3$ is different from H, u is different from 1;

and pharmaceutically acceptable salts thereof.

Further subject of the present invention are the intermediates of general formula (II) hereinafter reported, the preparation processes for compounds of the above reported formula (I), the pharmaceutical compositions comprising them and their use in PDT and/or BNCT therapy.

Features and advantages of the present invention will be illustrated in details in the following description.

DETAILED DESCRIPTION OF THE INVENTION

Figure 1:
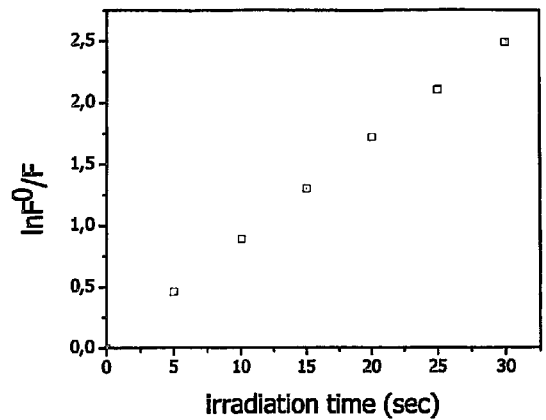
FIG. 1: Photooxydation kinetics of 9,10-dimethylantracene (DMA) with tetrasubstituted boronated phhalocyanine prepared as described in Example 21 in DMF, after irradiation with 600-700 nm light at 100 mW/cm$^2$.

The present invention allows one to meet the above-mentioned requirements thanks to the compounds of formula (I) as above described.

On the contrary to what it is expected from the molecular structure and taking into consideration that both side chains number and/or bulkiness may interfere with optimal behaviour of the phthalocyanines macrocycle, by reducing the in vivo stability, the photodynamic features and the tumour-localizing properties, the Applicant has surprisingly found that the products subject of the present invention maintain the physical-chemical properties linked with the photosensitising features, particularly the wavelength, the fluorescence and quantum yield of singlet-oxygen production and the molar extinction coefficient. These products are also able to efficiently localize into tumours after systemic administration as well and can efficiently sensitize a hard-to-treat tumour, such as the pigmented melanoma, to both PDT and BNCT.

The presence of at least one substituent bearing at least two or more $^{11}$B or $^{10}$B isotopes clusters on the peripheral position of the macrocycle, neither interferes with cellular localization estimated on model cells, nor with the photobleaching processes, while it provides optimal characteristics.

Thanks to the products herein described, a substantial improvement of the specific toxicity on the therapeutic target is achieved for synergic effect, while sparing healthy cells. Cells may thus be inactivated through a photodynamic mechanism related to the phtahlocyanine and is also possible to inactivate tumour cells by means of BNCT, due to the presence of a sufficiently large number of boron atoms on the phthalocyanine carrier, as well as to the sufficiently high affinity of the boronated phthalocyanine for an experimental tumour model.

Resistance associated to cells mutation and/or transformation as a result of PDT/BNCT combined action is not expected; in fact the cellular inactivation due to photodynamic process is the result of a cellular membrane damage without involvement of the nuclear material; moreover, the inactivation promoted by BNCT is too energetic to induce the selection of radioresistant cell clones.

Preferred compounds according to the present invention are the compounds of is formula (I) in which Me is Zn.

The present compounds of formula (I) may carry from one to eight groups bearing $^{11}B$ or $^{10}B$ Isotopes in the alpha or beta positions on the phthalocyanine molecule, preferably at the positions 1(4),8(11),15(18),22(25) or 2(3),9(10),16(17), 23(24). Preferred are the present compounds (I) wherein $R_1=R_2=H$ and $R=R_3$ are different from H. Preferably, in the present compounds (I) G is O, X is phenyl and Y Is $CH_2$. The compounds of the present invention can be prepared according to reaction schemes known in organic chemistry, for example by using one of the following general procedures:

a) process comprising the tetramerization of the functionalised phthalonitriles of general formula (II)

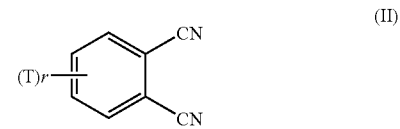

wherein T is a group $(G)_s$-$(X)_t$-$(Y-Z)_u$ wherein G, X, Y, Z, s, t, and u are as defined above; and r is 1, 2; alone or in the presence of dicyanobenzene, possibly in the presence of a reactant suitable for introducing the metal into the phthalocyanine nucleus, thus obtaining a compound of formula (I). In the following Scheme 1 the tetramerization of compound (II), alone or with dicyanobenzene, in the presence of $Zn(OAc)_2$ is illustrated.

Scheme 1:

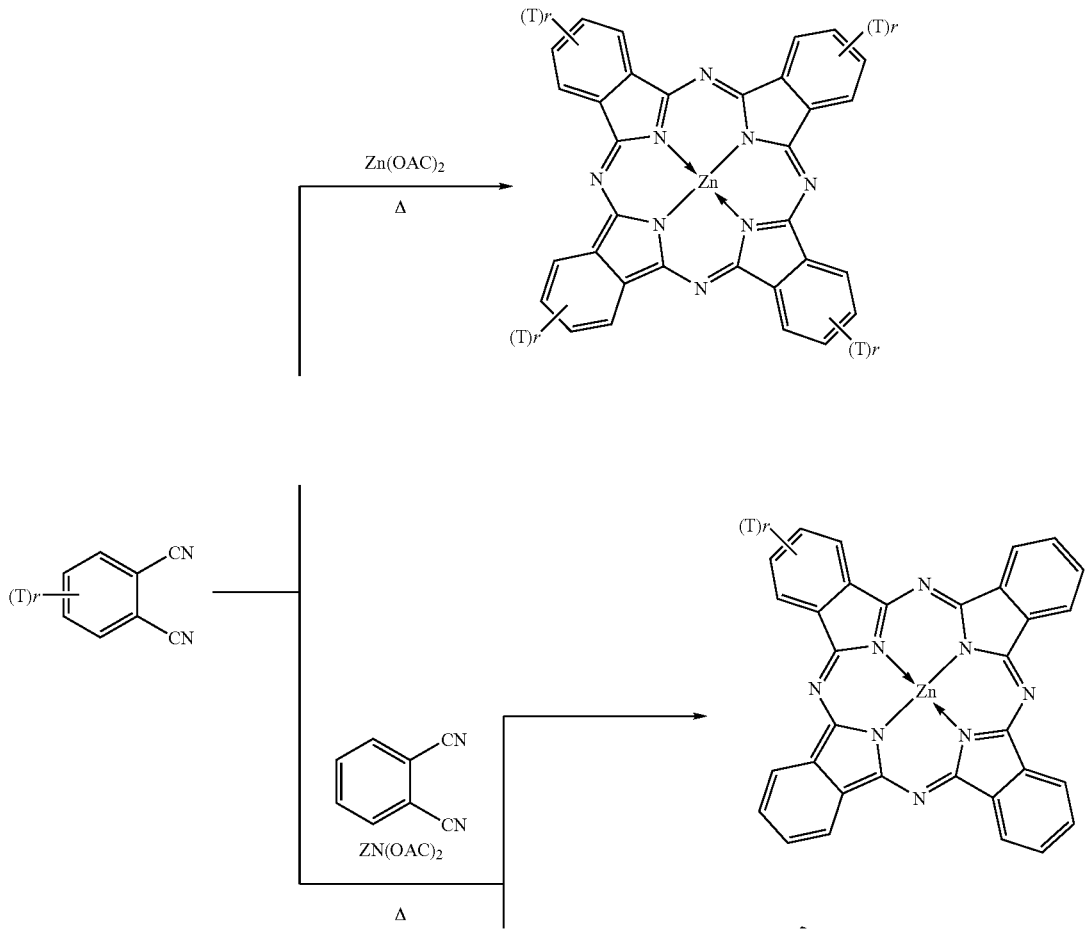

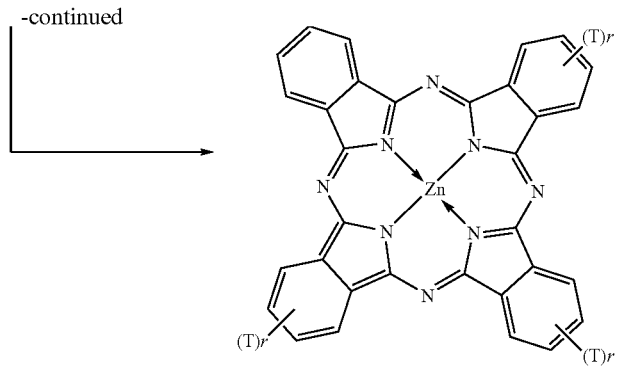

b) process comprising the insertion of boronated chains as above defined onto previously functionalised metal-phthalocyanines bearing from 1 to 8 functional groups, by coupling reactions known in the state of the art.

The phthalonitriles of formula (II) reported above can be prepared starting from commercially available materials according to the following Scheme 2.

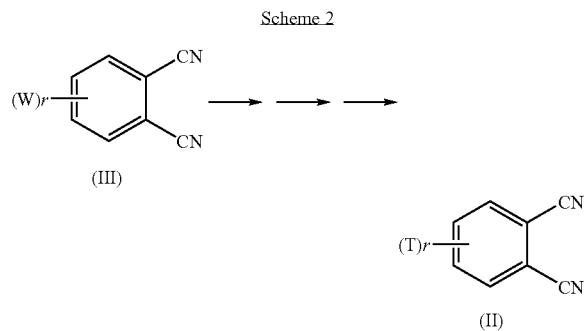

wherein T and r are as defined above, and W is selected from the group consisting of $NO_2$, $NH_2$, Cl, Br, I, OH, and $(G)_s$-$(X)_t$-$(P)_u$, wherein G, X, s, t and u are as defined above, and P is selected from the group consisting of Br, Cl, O, C≡CH, CHO, COOH, $NH_2$, OH, methansulfonyloxy, tosyloxy and Y, wherein Y is as defined above.

The compounds of formula (III) wherein W is selected from the group consisting of $NO_2$, $NH_2$, Cl, Br, I and OH are commercially available, whereas the remaining compounds of formula (III) can be prepared starting from these commercial products by means of procedures known in the art.

The schemes reported below show the synthetic pathway followed for the preparation of several boronated phthalocyanines of formula (I) according to the invention (Scheme 4, 6, 7 and 9), and of the corresponding intermediates (Scheme 3, 5 and 8). The schemes are reported to illustrate, but are not limited at, examples of the synthetic procedures suitable to obtain the present compounds of formula (I) and (II), as above defined.

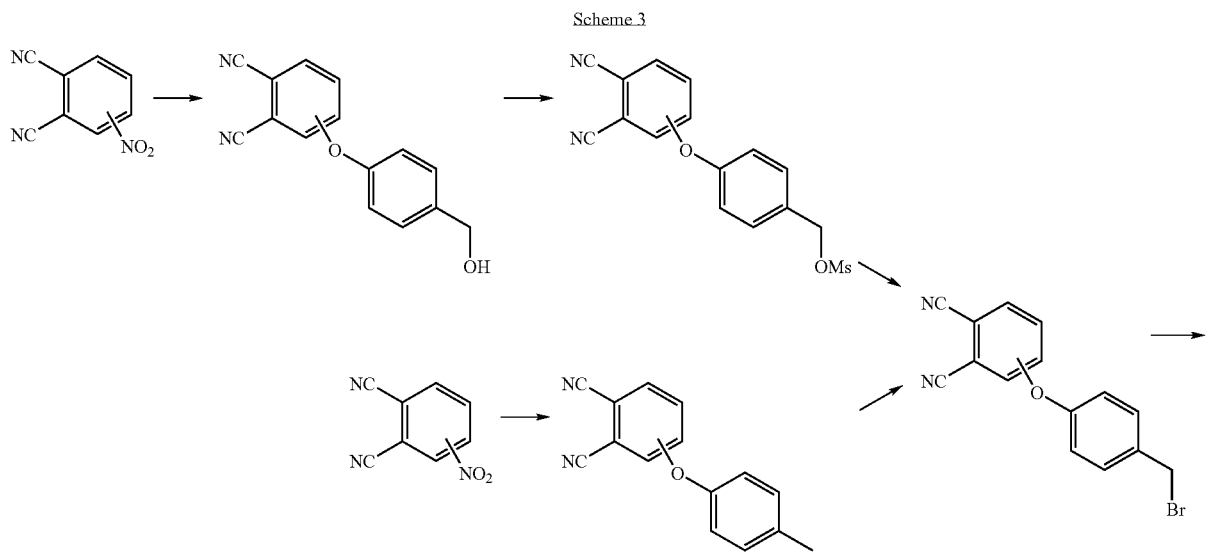

-continued
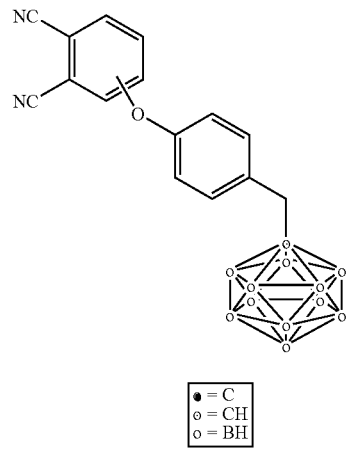
Scheme 4
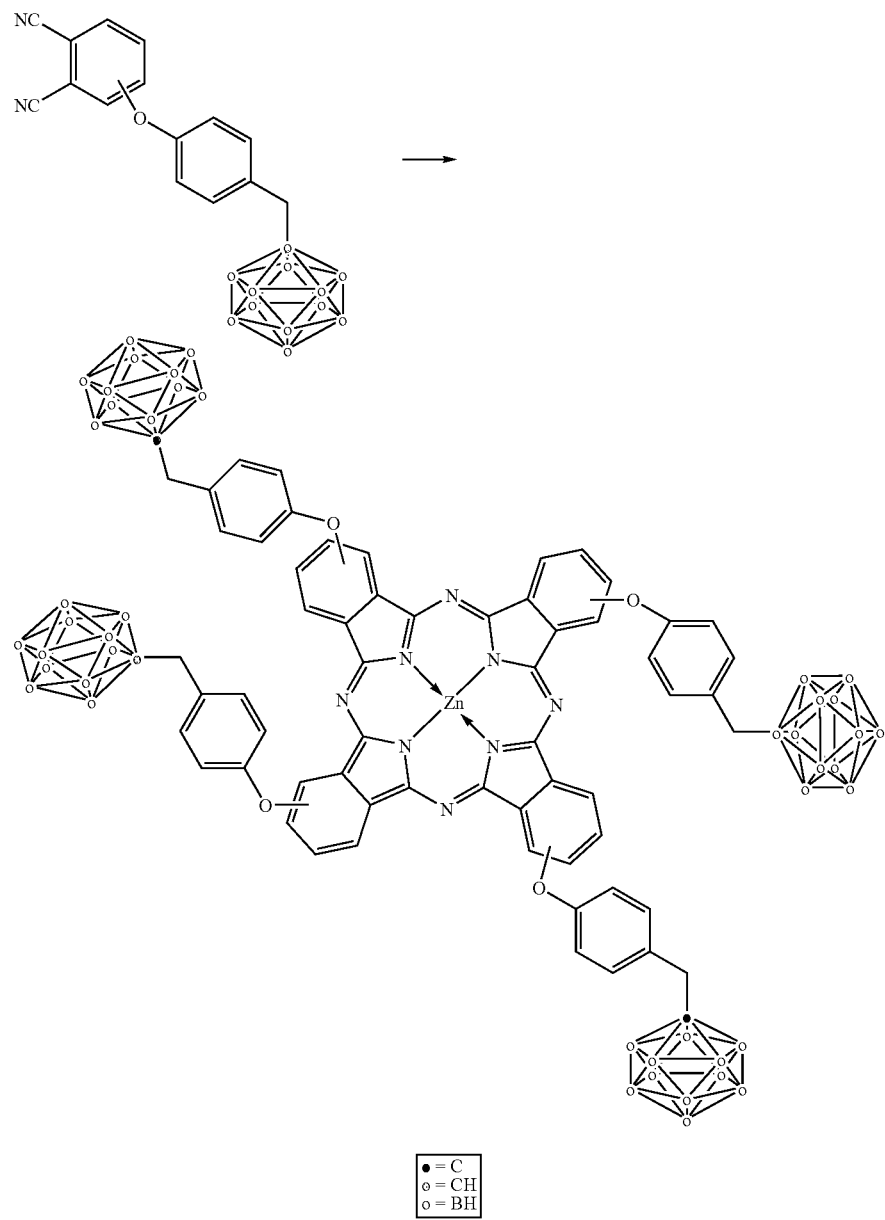

Scheme 5
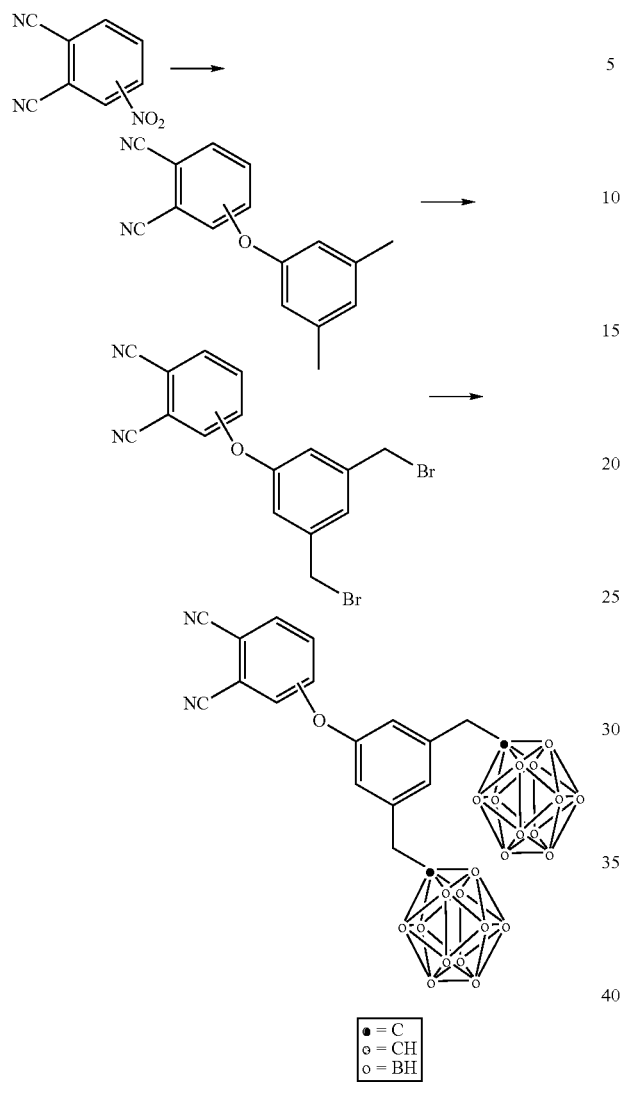
Scheme 6
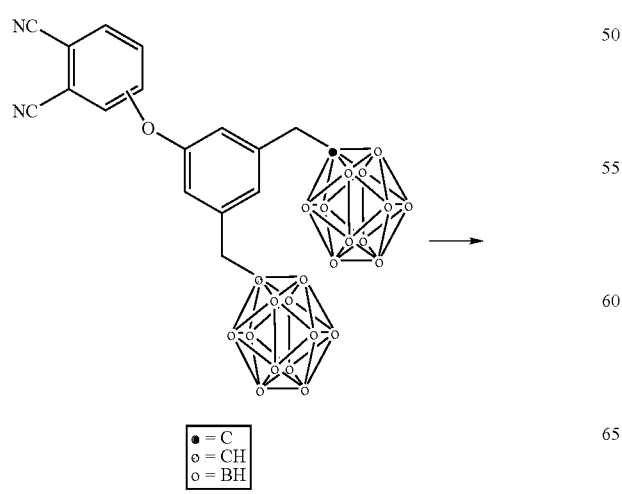

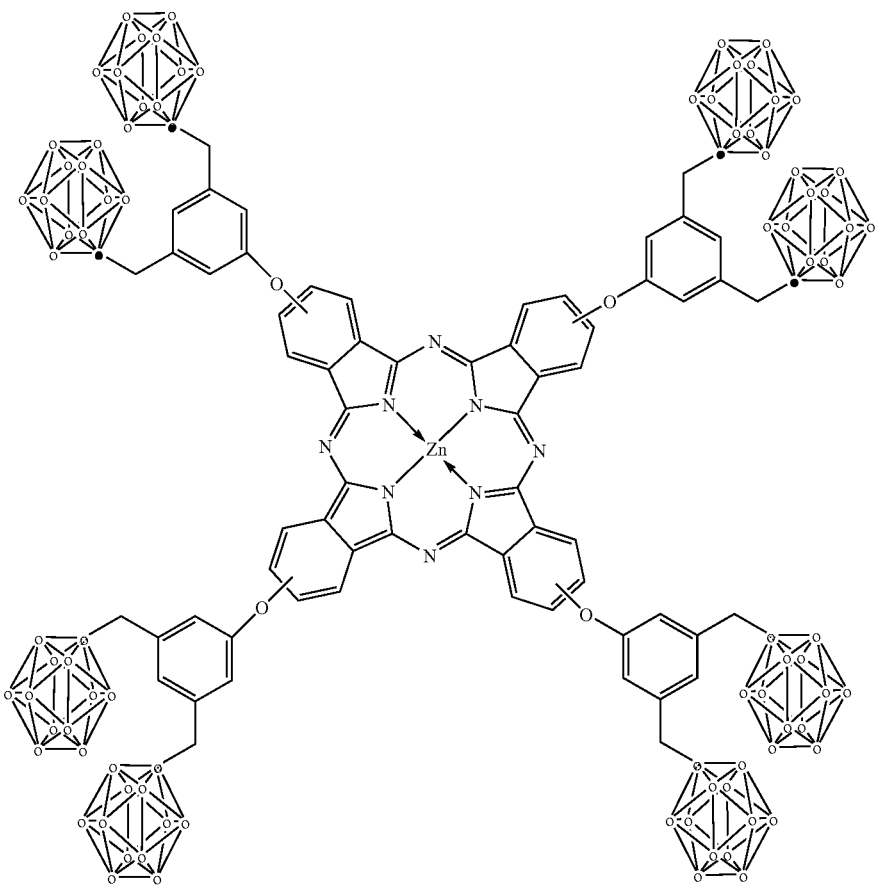
40
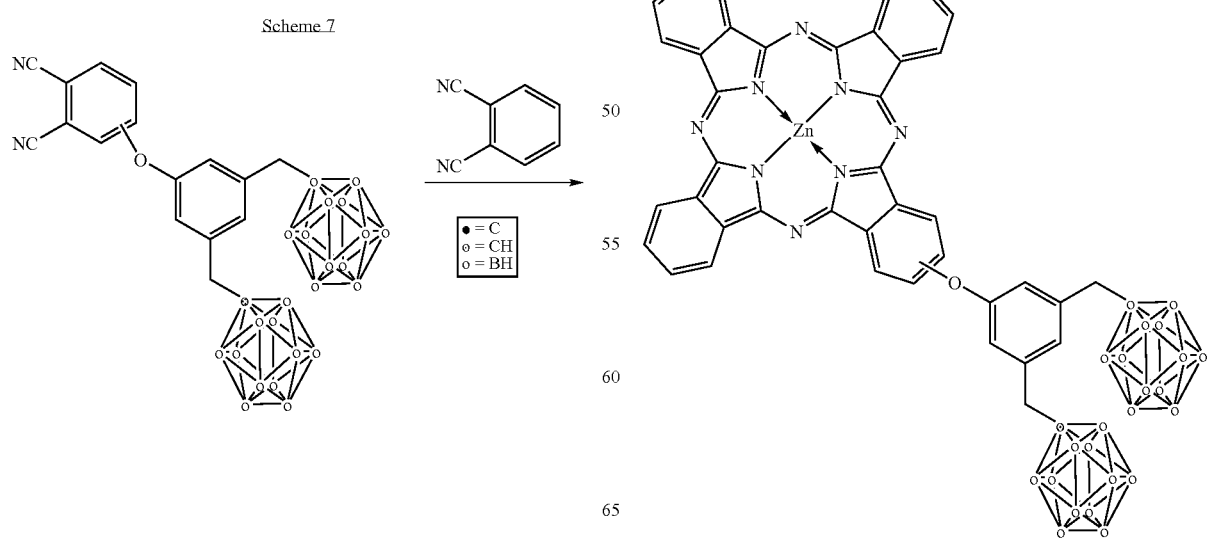
Scheme 7
● = C
o = CH
○ = BH

Scheme 8

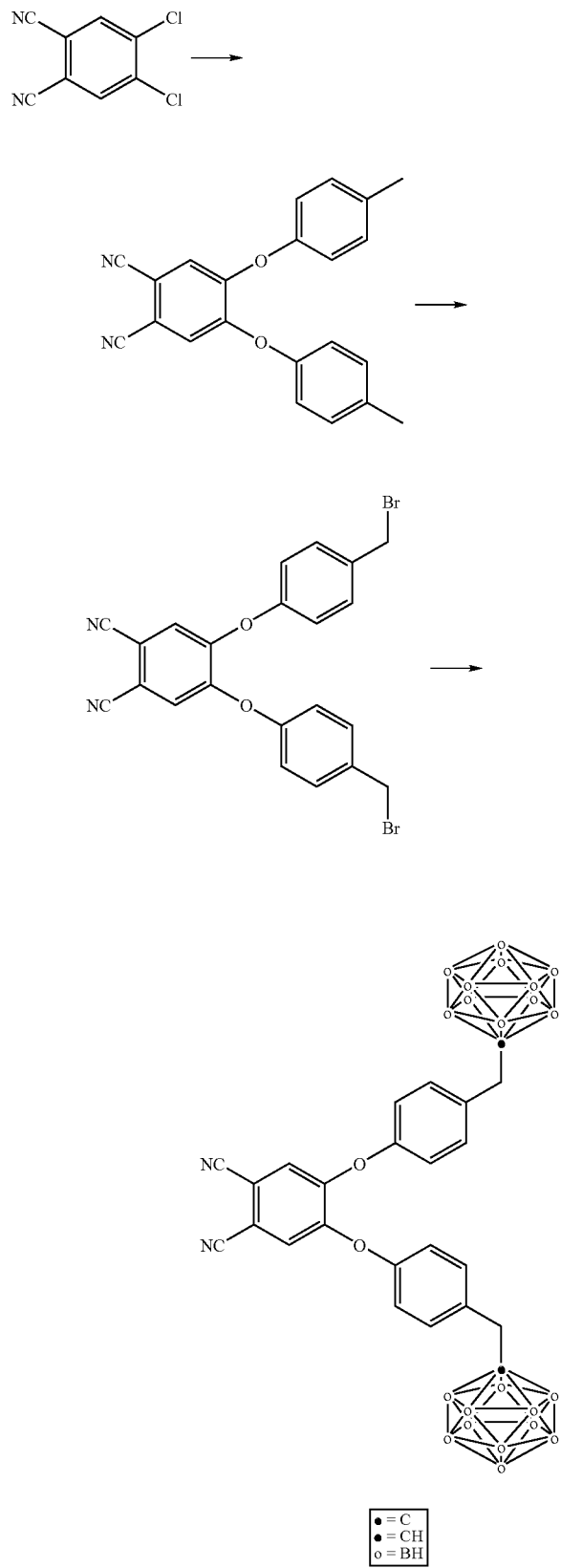

Scheme 9

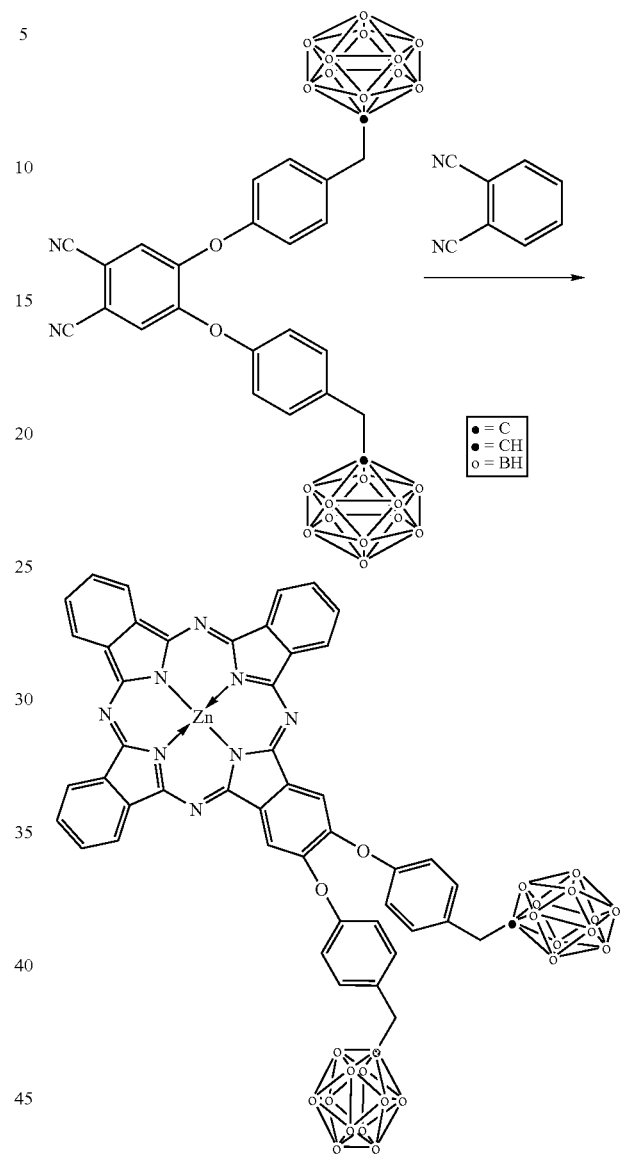

The following examples are reported as a non-limiting illustration of the invention.

EXAMPLE 1

Synthesis of 3-[4-(methansulfonylmethyl)phenoxy]phthalonitrile

To a solution of 3-[4-(hydroxymethyl)phenoxy]phthalonitrile (900 mg, 3.9 mmol) prepared according to procedures described in literature, and triethylamine (0.75 ml, 5.8 mmol) in anhydrous $CH_2Cl_2$ (50 ml), kept at 0° C. under stirring and in an inert atmosphere, methylsulfonylchloride was added (0.33 ml, 4.3 mmol). The mixture was stirred at 0° C. for 1 hour, then it was diluted with $CH_2Cl_2$ (50 ml) and washed with 1% HCl solution (60 ml), then with brine (50 ml), the organic layer was dried on $Na_2SO_4$ and the solvent was evaporated. 1.1 g (93%) of the title compound were obtained as a viscous fluid that crystallized on standing.

¹H-NMR (300 MHz, CDCl$_3$): 7.69 (1H, dd, J$_1$=J$_2$=8.4 Hz), 7.53-7.49 (3H, m), 7.15-7.11 (3H, m), 5.26 (2H, s), 3.01 (3H, s) δ

¹³C-NMR (75 MHz, CDCl$_3$): 160.46, 154.98, 134.90, 131.65, 131.43, 127.84, 121.35, 120.79, 117.64, 115.28, 112.80, 106.89, 70.48, 38.52 δ

EI$^+$-MS: m/z 328 [(C$_{15}$H$_{10}$N$_2$O$_4$S)]$^+$, 250 [(C$_{15}$H$_{10}$N$_2$O$_4$S)—CH$_3$SO$_2$]$^+$, 233 [(C$_{15}$H$_{10}$N$_2$O$_4$S)—CH$_3$SO$_3$]$^+$

EXAMPLE 2

Synthesis of 4-[4-(methansulfonylmethyl)phenoxy]phthalonitrile

To a solution of 4-[4-(hydroxymethyl)phenoxy]phthalonitrile (1.0 g, 3.9 mmol) prepared according to procedures described in literature, and triethylamine (0.80 ml, 5.8 mmol) in anhydrous CH$_2$Cl$_2$ (50 ml), kept at 0° C. under stirring and in an inert atmosphere, methylsulfonylchloride was added (0.33 ml, 4.3 mmol). The mixture was stirred at 0° C. for 1 hour, then ft was diluted with CH$_2$Cl$_2$ (50 ml) and washed with 1% HCl solution (60 ml), then with brine (50 ml), the organic layer was dried on Na$_2$SO$_4$ and the solvent was evaporated. 1.2 g (92%) of the title compound were obtained as a viscous fluid that crystallised on standing.

¹H-NMR (300 MHz, CDCl$_3$): 7.75 (1H, d, J=8.4 Hz), 7.53 (2H, d, J=8.7 Hz), 7.30-7.24 (2H, m), 7.12 (2H, d, J=8.7 Hz), 5.26 (2H, s), 3.03 (3H, s) δ

¹³C-NMR (75 MHz, CDCl$_3$): 161.50, 154.66, 135.82, 131.81, 131.52, 122.04, 121.95, 121.17, 917.93, 115.59, 115.16, 109.64, 70.22, 38.46 δ

EI$^+$-MS: m/z 250 [(C$_{15}$H$_{10}$N$_2$O$_4$S)—CH$_3$SO$_2$]$^+$, 233 [(C$_{15}$H$_{10}$N$_2$O$_4$S)—CH$_3$SO$_3$]$^+$

EXAMPLE 3

Synthesis of 3-[4-(bromomethyl)phenoxy]phthalonitrile

To a solution of 3-[4-(methansulfonylmethyl)phenoxy]phthalonitrile (1.1 g, 3.1 mmol) prepared according to Example 2, in anhydrous THF (15 ml) kept in an inert atmosphere, LiBr (0.4 g, 4.6 mmol) was added. The solution was refluxed for 1 hour, during which a white precipitate formed, then it was allowed to cool at room temperature. The white precipitate was filtered off and the solvent was evaporated. From the crude mixture the desired product was isolated by filtration on silica gel (eluent: chloroform). (900 mg, 93%).

¹H-NMR (300 MHz, CDCl$_3$): 7.59 (1H, dd, J$_1$=J$_2$=8.4 Hz), 7.49-7.63 (3H, m), 7.14-7.06 (3H, m), 4.51 (2H, s) δ

¹³C-NMR (75 MHz, CDCl$_3$): 160.67, 154.05, 136.07, 134.93, 131.57, 127.68, 121.20, 120.80, 117.50, 115.36, 112.91, 106.52, 32.59 δ

EI$^+$-MS: m/z 313 [C$_{15}$H$_{10}$N$_2$OBr]$^+$, 233 [(C$_{15}$H$_{10}$N$_2$OBr)—Br]$^+$ m.p.: 130-132° C.

Anal. Calcd. for C$_{15}$H$_{10}$N$_2$OBr (%): C (57.53), H (2.90), N (8.95); Found (%): C (57.40), H (2.92), N (8.96)

EXAMPLE 4

Synthesis of 4-[4-(bromomethyl)phenoxy]phthalonitrile

To a solution of 4-[4-(methansulfonylmethyl)phenoxy]phthalonitrile (1.2 g, 3.3 mmol) prepared according to Example 2, in anhydrous THF (15 ml) kept in an inert atmosphere, LiBr (0.4 g, 4.6 mmol) was added. The solution was refluxed for 1 hour, during which a white precipitate formed, then it was allowed to cool at room temperature. The white precipitate was filtered off and the solvent was evaporated. From the crude mixture the desired product was isolated by filtration on silica gel (eluent: chloroform). (1.0 g, 95%)

¹H-NMR (300 MHz, CDCl$_3$): 7.74 (1H, d, J=8.4 Hz), 7.49 (2H, d, J=8.6 Hz), 7.30-7.24 (2H, m), 7.05 (2H, d, J=8.6), 4.52 (2H, s) δ

¹³C-NMR (75 MHz, CDCl$_3$): 161.63, 153.80, 136.20, 135.73, 131.68, 121.97, 121.88, 121.08, 117.97, 115.54, 115.11, 109.44, 32.39 δ

EI$^+$-MS: m/z 233 [(C$_{15}$H$_{10}$N$_2$OBr)—Br]$^+$ m.p.: 100.8-102.2° C.

Anal. Calcd. for C$_{15}$H$_{10}$N$_2$OBr (%): C (57.53), H (2.90), N (8.95); Found (%): C (57.86), H (2.79), N (8.65)

p.f.: 100.8-102.2° C.

EXAMPLE 5

Synthesis of 3-{4-[($^{11}$B-o-carboran-1-yl)methyl]phenoxy}phthalonitrile n-butyl lithium (1.40 ml, 1.6M in hexanes, 2.2 mmol) was added dropwise to a solution of 1,2-closo-carborane (366 mg, 2.0 mmol) in anhydrous THF (10 ml) kept in an inert atmosphere at −78° C. The solution was stirred at −78° C. for 10 min. then it was kept at room temperature for 40 min. and cooled again at −78° C., and 3-[4-(bromomethyl)phenoxy]phthalonitrile (500 mg, 1.6 mmol), prepared according to Example 3. The mixture was stirred for 1 hour while being warmed to room temperature, then it was quenched with water, and the mixture was extracted with ethyl acetate. The organic layer was washed with brine (30 ml×2) then it was dried on Na$_2$SO$_4$, and the solvent was evaporated. The crude product was purified by flash chromatography (eluent: petroleum spirit/ethyl acetate=3/1) to yield 333 mg (55%) of the title compound.

¹H-NMR (300 MHz, CDCl$_3$): 7.63 (1H, dd, J$_1$=J$_2$=7.9 Hz), 7.51 (1H, d, J=7.9 Hz), 7.26-7.22 (2H, m), 7.14-7.08 (3H, m), 3.54 (2H, s), 3.35 (1H, bs), 2.94-1.25 (10H, bm) δ

¹³C-NMR (75 MHz, CDCl$_3$): 160.39, 154.40, 134.81, 132.53, 132.24, 127.84, 121.34, 120.82, 117.77, 115.20, 112.67, 74.26, 59.94, 43.10 δ (selected data)

EI$^+$-MS: m/z 376 [C$_{17}$H$_{20}$N$_2$OB$_{10}$]$^+$, 233 [(C$_{17}$H$_{20}$N$_2$OB$_{10}$)—C$_2$B$_{10}$H$_{11}$]$^+$ m.p.: 182-184° C.

Anal. Calcd. for C$_{17}$H$_{20}$N$_2$OB$_{10}$ (%): C (54.24), H (5.36), N (7.44); Found (%): C (54.10), H (5.30), N (7.18).

EXAMPLE 6

Synthesis of 4-{4-[($^{11}$B-o-carboran-1-yl)methyl]phenoxy}phthalonitrile n-butyl lithium (1.40 ml, 1.6M in hexanes, 2.2 mmol) was added dropwise to a solution of 1,2-closo-carborane (366 mg, 2.0 mmol) in anhydrous THF (10 ml) kept in an inert atmosphere at −78° C. The solution was stirred at −78° C. for 10 min. then it was kept at room temperature for 40 min. and cooled again at −78° C., and 4-[4-(bromomethyl)phenoxy]phthalonitrile (500 mg, 1.6 mmol), prepared according to Example 4. The mixture was stirred for 1.5 hours while being warmed to room temperature, then it was quenched with water, and the mixture was extracted with ethyl acetate. The organic layer was washed with brine (30 ml×2) then it was dried on $Na_2SO_4$, and the solvent was evaporated. The crude product was purified by flash chromatography (eluent: petroleum spirit/ethyl acetate=3/1) to yield 287 mg (48%) of the title compound.

$^1$H-NMR (300 MHz, $CDCl_3$): 7.76 (1H, d, J=9.0Hz), 7.31-7.23 (4H, m), 7.07 (2H, d, J=8.4 Hz), 3.55 (2H, s), 3.37 (1H, bs), 2.95-1.39 (10H, bm) δ

$^{13}$C-NMR (75 MHz, $CDCl_3$): 161.36, 154.05, 135.80, 132.69, 132.40, 122.13, 121.99, 121.16, 118.04, 115.49, 115.08, 109.67, 74.22, 59.92, 43.10 δ

$EI^+$-MS: m/z 376 $\mathbf{u}^+$, 233 $[(C_{17}H_{20}N_2OB_{10})-C_2B_{10}H_{11}]$ m.p.: 183.0-185.0° C.

Anal. Calcd. for $C_{17}H_{20}N_2OB_{10}$ (%): C (54.24), H (5.36), N (7.44); Found (%): C (54.50), H (5.08), N (7.70)

EXAMPLE 7

Synthesis of 3-{4-[($^{10}$B-o-carboran-1-yl)methyl]phenoxy}phthalonitrile

Starting from 1,2-closo-carborane (235 mg, 1.7 mmol) and 3-[4-(bromomethyl)phenoxy]phthalonitrile (500 mg, 1.6 mmol), prepared as showed in Example 3, 300 mg (yield=47%) of desired compound are obtained, following the procedure described in Example 5.

$^1$H-NMR (300 MHz, $CDCl_3$): 7.63 (1H, dd, $J_1$=$J_2$=7.8 Hz), 7.51 (1H, d, J=7.8 Hz), 7.26-7.22 (2H, m), 7.14-7.08 (3H, m), 3.54 (2H, s), 3.38 (1H, bs), 2.50-1.82 (10H, bm) δ

$^{13}$C-NMR (75 MHz, $CDCl_3$): 160.38, 154.37, 134.84, 132.54, 132.24, 127.84, 121.33, 120.84, 117.75, 115.22, 112.71, 106.92, 74.32, 59.98, 43.11 δ

$ESI^-$-MS: m/z 367 $[C_{17}H_{20}N_2OB_{10}]^-$ p.f.: 179-181° C.

EXAMPLE 8

Synthesis of 3-[3,5-bis-(bromomethyl)phenoxy]phthalonitrile

N-bromosuccinimide (790 mg, 4.4 mmol) was dissolved in dichloroethane and the mixture was warmed to reflux. 3-[3,5-bis-(methyl)phenoxy]phthalonitrile (500 mg, 2 mmol), prepared according to procedures described in literature, and a catalytic amount of benzoyl peroxide were added and the mixture was refluxed for 1.15 hours. After cooling to room temperature, the reaction mixture was diluted with dichloromethane, washed with saturated solution of $NaHCO_3$ and water and dried on $Na_2SO_4$. The solvent was evaporated and the crude was purified by flash chromatography (eluent: petroleum spiritlethyl acetate=4/1) to yield 350 mg (43%) of the title compound.

$^1$H-NMR (300 MHz, $CDCl_3$): 7.63 (1H, dd, $J_1$=$J_2$=8 Hz), 7.52 (1H, d, J=8 Hz), 7.33 (1H, s), 7.15 (1H, d, J=8 Hz), 7.08 (2H, s), 4.45 (4H, s) δ

EXAMPLE 9

Synthesis of 4-[3,5-bis-(bromomethyl)phenoxy]phthalonitrile

N-bromosuccinimide (394 mg, 2.2 mmol) was dissolved in dichloroethane. The mixture was warmed to reflux, 4-[3,5-bis-(methyl)phenoxy]phthalonitrile (250 mg, 1 mmol) prepared according to procedures described in literature, and a catalytic amount of benzoyl peroxide were added and the mixture was refluxed for 1 hour. After cooling to room temperature, the reaction mixture was diluted with dichloromethane, washed with saturated solution of $NaHCO_3$ and water and dried on $Na_2SO_4$. The solvent was evaporated and the crude was purified by flash chromatography (eluent: petroleum spirit/ethyl acetate=4/1) to obtain 150 mg (yield=37%) of the title compound.

$^1$H-NMR (300 MHz, $CDCl_3$): 7.76 (1H, d J=8 Hz), 7.35-7.25 (3H, m), 7.06 (2H, s), 4.45 (4H, s) δ

EXAMPLE 10

Synthesis of 3-{3,5-[bis-(11B-carboran-1-yl)methyl]phenoxy}phthalonitrile n-butyl lithium (0.97 ml, 1.6M in hexanes, 1.54 mmol) was added dropwise to a solution of 1,2-closo-carborane (200 mg, 1.4 mmol) in anhydrous THF (10 ml) kept in an inert atmosphere at −78° C. The solution was stirred at −78° C. for 10 min. then it was kept at room temperature for 40 min. and cooled again at −78° C., and 3-[3,5-bis-(bromomethyl)phenoxy]phthalonitrile (227 mg, 0.56 mmol) prepared according to Example 8. The mixture was stirred for 1 hour while being warmed to room temperature, then it was quenched with water, and the mixture was extracted with ethyl acetate. The organic layer was washed with brine (30 ml×2) then it was dried on $Na_2SO_4$, and the solvent was evaporated. The crude product was purified by flash chromatography (eluent: petroleum spirit/ethyl acetate=4/1 to 1/2) to obtain 58 mg (yield=19%) of the title compound.

$^1$H-NMR (300 MHz, $CDCl_3$): 7.69 (1H, dd, $J_1$=$J_2$-8 Hz), 7.57 (1H, d, J=8 Hz), 7.12 (1H, d, J=8 Hz), 6.88-6.86 (3H, m), 3.52 (4H, s), 3.45 (2H, bs), 3.00-1.00 (10H, bm) δ

$ESI^+$-MS: m/z 532 $[C_{20}H_{32}N_2OB_{20}]^+$

EXAMPLE 11

Synthesis of 4-{3,5-[bis-($^{11}$B-o-carboran-1-yl)methyl]phenoxy}phthalonitrile n-butyl lithium (0.97 ml, 1.6M in hexanes, 1.54 mmol) was added dropwise to a solution of 1,2-closo-carborane (200 mg, 1.4 mmol) in anhydrous THF (10 ml) kept in an inert atmosphere at −78° C. The solution was stirred at −78° C. for 10 min. then it was kept at room temperature for 40 min. and cooled again at −78° C., and 4-[3,5-bis-(bromomethyl)phenoxy]phthalonitrile (227 mg, 0.56 mmol) prepared according to Example 9. The mixture was stirred for 1 hour while being warmed to room temperature, then it was quenched with water, and the mixture was extracted with ethyl acetate. The organic layer was washed with brine (30 ml×2) then it was dried on $Na_2SO_4$, and the solvent was evaporated. The crude product was purified by flash chromatography (eluent: petroleum spiritlethyl acetate=1/1) to obtain 82 mg (yield=28%) of the title compound.

$^1$H-NMR (300 MHz, $CDCl_3$): δ 7.79 (1H, d, J=8 Hz), 7.29-7.21 (2H, m), 6.87 (3H, s), 3.52 (4H, s), 3.45 (2H, bs), 3.10-1.00 (10H, bm)

$ESI^+$-MS: m/z 532 $[C_{20}H_{32}N_2OB_{20}]^+$

According with the two alternative procedures reported above in Examples 1-11, the following compounds were also obtained:

EXAMPLE 12

3-{3,5-[bis-($^{10}$B-o-carboran-1-yl)methyl]phenoxy}phthalonitrile $^1$H-NMR (300 MHz, CDCl$_3$): 7.69 (1H, dd, J$_1$=J$_2$=8.0 Hz), 7.57 (1H, d, J=8.0 Hz), 7.12 (1H, d, J=8.0 Hz), 6.88-6.86 (3H, m), 3.52 (4H, s), 3.40 (2H, bs), 2.750-1.20 (10H, bm) δ

ESI$^+$-MS: m/z 516 [C$_{20}$H$_{32}$N$_2$OB$_{20}$]$^+$

EXAMPLE 13

4-{3,5-[bis-($^{10}$B-o-carboran-1-yl)methyl]phenoxy}phthalonitrile $^1$H-NMR (300 MHz, CDCl$_3$): 7.79 (1H, d, J=8.0 Hz), 7.29-7.21 (2H, m), 6.87 (3H, s), 3.52 (4H, s), 3.39 (2H, bs), 2.97-1.13 (10H, bm) δ

ESI$^+$-MS: m/z 516 [C$_{20}$H$_{32}$N$_2$OB$_{20}$]$^+$

EXAMPLE 14

4-{2,4,6-[tris($^{11}$B-o-carboran-1-yl)methyl]phenoxy}phthalonitrile $^1$H-NMR (300 MHz, CDCl$_3$): 7.65 (1H, d, J=8.0 Hz), 7.40 (2H, s), 7.07-7.05 (3H, m), 3.61, (4H, s), 3.52 (2H, s), 3.43 (2H, bs), 3.40 (1H, bs), 2.84-1.76 (30H, bm) δ

ESI$^+$-MS: m/z 688 [C$_{23}$H$_{44}$N$_2$OB$_{30}$]$^+$

EXAMPLE 15

3-{2,4,6-[tris($^{11}$B-o-carboran-1-yl)methyl]phenoxy}phthalonitrile $^1$H-NMR (300 MHz, CDCl$_3$): 7.67 (1H, dd, J$_1$=J$_2$=8.0 Hz), 7.60 (1H, d, J=8.0 Hz), 7.40 (2H, s), 7.12 (1H, d, J=8.0 Hz), 3.64, (4H, s), 3.54 (2H, s), 3.41 (2H, bs), 3.38 (1H, bs), 2.80-1.77 (30H, bm) δ

ESI$^+$-MS: m/z 688 [C$_{23}$H$_{44}$N$_2$OB$_{30}$]$^+$

EXAMPLE 16

4-{2,4,6-[tris(10B-o-carboran-1-yl)methyl]phenoxy}phthalonitrile $^1$H-NMR (300 MHz, CDCl$_3$): 7.65 (1H, d, J=8.0 Hz), 7.40 (2H, s), 7.07-7.05 (3H, m), 3.61, (4H, s), 3.52 (2H, s), 3.40 (2H, bs), 3.36 (1H, bs), 2.75-1.79 (30H, bm) δ

ESI$^+$-MS: m/z 664 [C$_{23}$H$_{44}$N$_2$OB$_{30}$]$^+$

EXAMPLE 17

3-{2,4,6-[tris($^{10}$B-o-carboran-1-yl)methyl]phenoxy}phthalonitrile $^1$H-NMR (300 MHz, CDCl$_3$): 7.67 (1H, dd, J$_1$=J$_2$=8.0 Hz), 7.60 (1H, d, J=8.0 Hz), 7.40 (2H, s), 7.12 (1H, d, J=8.0 Hz), 3.64, (4H, s), 3.51 (2H, s), 3.36 (2H, bs), 3.38 (1H, bs), 2.80-1.77 (30H, bm) δ

ESI$^+$-MS: m/z 664 [C$_{23}$H$_{44}$N$_2$OB$_{30}$]$^+$

EXAMPLE 18

4,5-bis-{4-[(11B-o-carboran-1-yl)methyl]phenoxy}phthalonitrile $^1$H-NMR (300 MHz, CDCl$_3$): 7.61 (2H, s), 7.37-7.24 (8H, m), 3.55 (4H, s), 3.32 (4H, bs), 2.91-1.06 (20H, bm) δ

ESI$^+$-MS: m/z 624 [C$_{26}$H$_{36}$N$_2$O$_2$B$_{20}$]$^+$

EXAMPLE 19

4,5-bis-{4-[($^{11}$B-o-carboran-1-yl)methyl]phenoxy}phthalonitrile $^1$H-NMR (300 MHz, CDCl$_3$): 7.61 (2H, s), 7.37-7.25 (8H, m), 3.55 (4H, s), 3.37 (4H, bs), 2.98-1.00 (20H, bm) δ

ESI$^+$-MS: m/z 608 [C$_{26}$H$_{36}$N$_2$O$_2$B$_{20}$]$^+$

EXAMPLE 20

4-{4-[($^{10}$B-o-carboran-1-yl)methyl]phenoxy}phthalonitrile $^1$H-NMR (300 MHz, CDCl$_3$): 7.76 (1H, d, J=9.0 Hz), 7.31-7.23 (4H, m), 7.07 (2H, d, J=8.4 Hz), 3.55 (2H, s), 3.37 (1H, bs), 2.95-1.39 (10H, bm) δ

ESI$^-$-MS: m/z 367 [C$_{17}$H$_{20}$N$_2$OB$_{10}$]$^-$

EXAMPLE 21

Synthesis of 1,8(11),15(18),22(25)-tetrakis-{[4-($^{11}$B-o-carboran-1-yl)methyl]phenoxy}-phthalocyaninate zinc(II)

A mixture of 3-{4-[($^{11}$B-o-carboran-1-yl)methyl]phenoxy}phthalonitrile (120 mg, 0.3 mmol), prepared according to Example 5, and Zn(OAc)$_2$ (59 mg, 0.3 mmol) was finely ground and heated to 200° C. in an inert atmosphere for 5.5 hours. The dark solid was then allowed to cool to room temperature, and was taken up in ethyl acetate. The suspension was filtered through celite and the solvent was evaporated. From the crude mixture the title compound was isolated by flash chromatography (eluent: petroleum spirit/THF 3/1 to 1/1). 54 mg of the title compound are obtained (yield=43%).

$^1$H-NMR (300 MHz, d$_6$-DMSO): 9.07 (d, J=7.2 Hz), 8.90-8.79 (m), 8.68-8.56 (m), 8.45 (d, J=7.2 Hz), 8.11-7.77 (m), 7.65 (d, J=7.8 Hz), 7.52-7.40 (m), 7.43-7.10 (m), 5.21-5.17 (m), 4.89 (bs), 3.68-3.59 (m), 3.48 (bs), 2.71-1.18 (bm) δ

$^{13}$C-NMR (75 MHz, d$_6$-DMSO): 159.80, 159.53, 159.40, 157.50, 157.43, 157.13, 156.97, 154.66, 154.48, 154.11, 153.97, 153.55, 153.36, 153.05, 152.82, 152.63, 151.75, 151.60, 151.42, 151.25, 150.42, 150.26, 141.47, 141.41, 141.34, 141.10, 140.93, 132.95, 132.24, 132.13, 132.07, 132.00, 131.65, 131.47, 131.25, 129.93, 129.84, 129.76, 129.10, 129.02, 128.79, 127.64, 127.53, 127.33, 123.79, 123.43, 123.21, 121.03, 120.67, 120.52, 120.21, 119.88, 119.66, 119.37, 119.11, 118.67, 118.09, 116.77, 116.69, 116.55, 77.45, 77.33, 63.59, 63.08, 42.18, 41.94 δ(selected data)

ESI$^+$-MS: m/z 1571 [C$_{68}$H$_{80}$N$_8$O$_4$B$_{40}$Zn]$^+$

UV-vis.(DMF): nm (%) 690 (100), 622 (16), 329 (18) ε$_{690}$=230000 M$^{-1}$ cm$^{-1}$

EXAMPLE 22

Synthesis of 2,9(10),16(17),23(24)-tetrakis-{[4($^{11}$B-o-carboran-1-yl)methyl]phenoxy}-phthalocyaninate zinc(II)

A mixture of 4-{4-[($^{11}$B-o-carboran-1-yl)methyl]phenoxy}phthalonitrile (70 mg, 0.2 mmol) prepared according to Example 6, and Zn(OAc)$_2$ (34 mg, 0.2 mmol) was finely ground and heated to 200° C. in an inert atmosphere for 5 hours. The dark solid was then allowed to cool to room temperature, and was taken up in ethyl acetate. The suspension was filtered through celite and the solvent was evaporated. From the crude mixture the title compound was isolated by flash chromatography (eluent: petroleum spirit/THF 3/1 to 1/1). 30 mg of the title compound are obtained (yield=40%).

$^1$H-NMR (300 MHz, d$_6$-DMSO) 8.98-8.91 (2H, m), 8.68-8.69 (2H, m), 8.45-8.41 (2H, m), 8.27-8.23 (2H, m), 7.79-7.40 (2H, m), 5.31 and 5.18 (4H, 2 bs), 3.76 and 3.68 (8H, 2 bs), 2.90-1.18 (40H, bm) δ

$^{13}$C-NMR (75 MHz, d$_6$-DMSO) 159.70, 158.71, 158.57, 157.34, 156.53, 156.41, 151.80, 140.03, 139.92, 132.99, 132.90, 132.68, 132.11, 124.40, 121.17, 119.98, 111.73, 77.45, 77.26, 63.76, 63.51, 42.15 δ (selected data)

ESI$^+$-MS: m/z 1571 [C$_{68}$H$_{80}$N$_8$ O$_4$B$_{40}$Zn]$^+$

UV-vis.(DMF): nm (%) 677 (100), 609 (17), 357 (34) δ$_{677}$=240000 M$^{-1}$ cm$^{-1}$

EXAMPLE 23

Synthesis of 1,8(11),15(18),22(25)-tetrakis-{[4-($^{10}$B-o-carboran-1-yl)methyl]phenoxy}phthalocyaninate zinc(II)

A mixture of 3-{4-[($^{10}$B-o-carboran-1-yl)methyl]phenoxy}phthalonitrile (200 mg, 0.5 mmol) prepared according to Example 7, and Zn(OAc)$_2$ (100 mg, 0.5 mmol) was finely ground and heated to 210° C. in an inert atmosphere for 4.5 hours. The dark solid was then allowed to cool to room temperature, and was taken up in ethyl acetate. The suspension was filtered through celite and the solvent was evaporated. From the crude mixture the title compound was isolated by flash chromatography (eluent: petroleum spirit/THF 3/1 to 1/1). 83 mg (yield=40%).

$^1$H-NMR (300 MHz, d$_6$DMSO): 9.13 (d, J=7.2 Hz), 9.01-8.98 (m), 8.68-8.56 (m), 8.75 (d, J=7.2 Hz), 8.65 (dd, J$_1$=J$_2$=7.2 Hz), 8.52 (d, J=7.2 Hz), 8.15-7.82 (m), 7.73 (d, J=7.5 Hz), 7.47-7.22 (m), 5.24-5.18 (m), 4.92 (bs), 3.68-3.64 (m), 3.50 (bs), 2.71-1.18 (bm) δ

$^{13}$C-NMR (75 MHz, d$_6$-DMSO): 159.81, 159.51, 159.39, 157.46, 157.39, 157.08, 154.46, 154.09, 153.94, 153.55, 153.07, 152.81, 150.38, 141.46, 141.39, 136.86, 132.95, 132.29, 132.06, 131.86, 131.67, 131.49, 129.95, 129.11, 128.78, 127.62, 127.50, 127.27, 121.07, 120.68, 120.52, 120.19, 116.65, 116.50, 77.50, 77.38, 63.65, 63.14, 42.17, 41.93 δ (selected data)

ESI$^+$-MS: m/z 1540 [C$_{68}$H$_{80}$N$_8$ O$_4$B$_{40}$Zn]$^+$

UV-vis.(DMF): nm (%) 690 (100), 622 (16), 326 (17) ε$_{690}$=250000 M$^{-1}$ cm$^{-1}$

EXAMPLE 24

Synthesis of 2,9(10),16(17),23(24)tetrakis-{[3,5-bis-($^{11}$B-o-carboran-1-yl)methyl]phenoxy}-phthalocyaninate zinc(II)

A mixture of 4-(3,5-bis-[($^{11}$B-o-carboran-1-yl)methyl]phenoxyphthalonltrile (83 mg, 0.15 mmol) prepared according to Example 11, and Zn(OAc)$_2$ (28 mg, 0.15 mmol) was finely ground and heated to 260° C. in an inert atmosphere for 4 hours. The dark solid was then allowed to cool to room temperature, and was taken up in ethyl acetate. The suspension was filtered through celite and the solvent was evaporated. From the crude mixture the title compound was isolated by flash chromatography (eluent: petroleum spirit(THF 1/1), thus obtaining 54 mg of the title compound (yield=43%).

$^1$H-NMR (300 MHz, d$_6$DMSO) 9.11-9.02 (4H, m), 8.55-8.48 (4H, m), 7.85-7.60 (4H, m), 7.36-7.06 (12H, m), 5.18 and 5.12 (8H, 2 bs), 3.73 and 3.68 (16H, 2 bs), 2.90-1.00 (80H, bm) δ

UV-vis.(DMF): nm (%) 677 (100), 610 (18), 355 (30)

ESI$^+$-MS: m/z 2197 [C$_{80}$H$_{129}$N$_8$O$_4$B$_{80}$Zn]$^+$

EXAMPLE 25

Synthesis of 1,8(11),15(18),22(25)-tetrakis-{[3,5-bis-($^{11}$B-o-carboran-1-yl)methyl]phenoxy}-phthalocyaninate zinc(II)

A mixture of 3-{3,5-bis-[($^{11}$B-o-carboran-1-yl)methyl]phenoxy}phthalonitrile (53 mg, 0.1 mmol) prepared according to Example 10, and Zn(OAc)$_2$ (19 mg; 0.1 mmol) was finely ground and heated to 260° C. in an inert atmosphere for 4 hours. The dark solid was then allowed to cool to room temperature, and was taken up in ethyl acetate. The suspension was filtered through celite and the solvent was evaporated. From the crude mixture the title compound was isolated by flash chromatography (eluent: petroleum spirit/THF 1/1), thus obtaining 54 mg of the title compound (yield=43%).

UV-vis.(DMF): nm (%) 690 (100), 624(15), 332 (27)

ESI$^+$-MS: m/z 2197 [C$_{80}$H$_{129}$N$_8$O$_4$B$_{80}$Zn]$^+$

According with the procedures reported in Examples 21-25, the following compounds were also obtained:

EXAMPLE 26

1,8(11),15(18),22(25)-tetrakis-{[3,5-bis-($^{10}$B-o-carboran-1-yl)methyl]phenoxy}-phthalocyaninate zinc(II)

ESI$^+$-MS: m/z 2136 [C$_{80}$H$_{129}$N$_8$O$_4$B$_{80}$Zn]$^+$

UV-vis (DMF): nm (%) 691 (100), 623 (17), 332 (21)

EXAMPLE 27

2,9(10),16(17),23(24)-tetrakis-{[3,5-bis-($^{10}$B-o-carboran-1-yl)methyl]phenoxy}-phthalocyaninate zinc(II)

ESI$^+$-MS: m/z 2136 [C$_{80}$H$_{129}$N$_8$O$_4$B$_{80}$Zn]$^+$

UV-vis (DMF): nm (%) 685 (100), 611 (16), 354 (40)

EXAMPLE 28

2,3,9,10,16,17,23,24-octakis-{[4-($^{11}$B-o-carboran-1-yl)methyl]phenoxy}-phthalocyaninate zinc(II)

ESI$^+$-MS: m/z 2564 [C$_{104}$H$_{144}$N$_8$O$_8$B80Zn]$^+$

UV-vis (DMF): nm (%) 680 (100), 613 (16), 361 (33)

EXAMPLE 29

2,3,9,10,16,17,23,24-octakis-{[4-($^{10}$B-o-carboran-1-yl)methyl]phenoxy}-phthalocyaninate zinc(II)

ESI$^+$-MS: m/z 2503 $[C_{104}H_{144}N_8O_8B_{80}Zn]^+$
UV-vis (DMF): nm (%) 680 (100), 615 (15), 360 (34)

EXAMPLE 30

2,9(10),16(17),23(24)-tetrakis{[4-($^{10}$B-o-carboran-1-yl)methyl]phenoxy}-phthalocyaninate zinc(II)

ESI$^+$-MS: m/z 1540 $[C_{68}H_{80}N_8O_4B_{40}Zn]^+$
UV-vis.(DMF): nm (%) 677 (100), 609 (20), 357 (33)

EXAMPLE 31

Synthesis of 2-{3,5-[bis-($^{11}$B-o-carboran-1-yl)methyl]phenoxy}}-phthalocyaninate zinc(II)

A mixture of 4-{3,5-bis-[($^{11}$B-o-carboran-1-yl)methyl]phenoxy}phthalonitrile (70 mg, 0.2 mmol) prepared according to Example 11, dicyanobenzene (77 mg, 0.6 mmol) and Zn(OAc)$_2$ (34 mg, 0.2 mmol) was finely ground and heated to 200° C. in an inert atmosphere for 5 hours. The dark solid was then allowed to cool to room temperature, and was taken up in THF. The suspension was filtered through celite and the solvent was evaporated. From the crude mixture the title compound was isolated by flash chromatography (eluent: petroleum spirit/THF 5/1 to 1/1). 15 mg of the title compound were obtained (yield=7.6%).

ESI$^+$-MS: m/z 983 $[C_{44}H_{45}N_8OB_{20}Zn]^+$
UV-vis (DMF): nm (%) 672(100), 609(16), 344(24)
UV-vis (DMF): nm (%) 680 (100), 613(16), 361(33)

According to the procedure described in Example 31, the following compounds where obtained:

EXAMPLE 32

2-{3,5-[bis-($^{10}$B-o-carboran-1-yl)methyl]phenoxy}-phthalocyaninate zinc(II)

ESI$^+$-MS: m/z 968 $[C_{44}H_{45}N_8OB_{20}Zn]^+$
UV-vis (DMF): nm (%) 672(100), 606(16), 344(25)

EXAMPLE 33

1-{3,5-[bis-(11B-o-carboran-1-yl)methyl]phenoxy}-phthalocyaninate zinc(II)

ESI$^+$-MS: m/z 983 $[C_{44}H_{45}N_8OB_{20}Zn]^+$
UV-vis (DMF): nm (%) 677(100), 335(21), 609(15)

EXAMPLE 34

1-{3,5-[bis-($^{10}$B-o-carboran-1-yl)methyl]phenoxy}-phthalocyaninate zinc(II)

ESI$^+$-MS: m/z 968 $[C_{44}H_{45}N_8OB_{20}Zn]^+$
UV-vis (DMF): nm (%) 678 (100), 610 (16), 336(23)

EXAMPLE 35

2,3-bis-{[4-($^{11}$B-o-carboran-1-yl)methyl]phenoxy}-phthalocyaninate zinc(II)

ESI$^+$-MS: m/z 1074 $[C_{50}H_{48}N_8O_2B_{20}Zn]^+$
UV-vis (DMF): nm (%) 672 (100), 606 (15), 342 (23)

EXAMPLE 36

2,3-bis-{[4-(10B-o-carboran-1-yl)methyl]phenoxy}-phthalocyaninate zinc(II)

ESI$^+$-MS: m/z 1059 $[C_{50}H_{48}N_8O_2B_{20}Zn]^+$
UV-vis (DMF): nm (%) 671 (100), 608 (13), 344 (23)

EXAMPLE 37

2-{2,4,6-[tris($^{11}$B-o-carboran-1-yl)methyl]phenoxy}-phthalocyaninate zinc(II)

ESI$^+$-MS: m/z 1140 $[C_{47}H_{57}N_8OB_{30}Zn]^+$
UV-vis (DMF): nm (%) 672 (100), 606 (16), 344 (24)

EXAMPLE 38

2-{2,4,6-[tris($^{10}$B-o-carboran-1-yl)methyl]phenoxy}-phthalocyaninate zinc(II)

ESI$^+$-MS: m/z 1117 $[C_{47}H_{57}N_8OB_{30}Zn]^+$
UV-vis (DMF): nm (%) 672 (100), 606 (16.0), 344 (25.1)

EXAMPLE 39

1-{2,4,6-[tris($^{11}$B-o-carboran-1-yl)methyl]phenoxy}-phthalocyaninate zinc(II)

ESI$^+$-MS: m/z 1117 $[C_{47}H_{57}N_8OB_{30}Zn]^+$
UV-vis (DMF): nm (%) 677 (100), 336 (23), 611 (15)

EXAMPLE 40

1-{2,4,6-[tris($^{10}$B-o-carboran-1-yl)methyl]phenoxy}-phthalocyaninate zinc(II)

ESI$^+$-MS: m/z 0.1117 $[C_{47}H_{57}N_8OB_{30}Zn]^+$
UV-vis (DMF): nm (%) 677 (100), 608 (14), 335 (22)

Assessment of Photodynamic Efficiency

Singlet oxygen is produced through an electron energy transfer from the phthalocyanines in their excited triplet state to molecular oxygen. For its high reactivity and its relatively long life time (in the microseconds time-scale, with consequent possibility of diffusion within relatively wide distance before decaying), it represents the main phototoxic intermediate in the photosensitising processes. Therefore, defining the photodynamic efficiency of these compounds through the measurement of the efficiency of singlet oxygen production is particularly useful. Measurement of singlet oxygen has been performed following the photooxidation kinetics of 9,10-dimethylantracene (DMA) spectrophotometrically; as reported in FIG. 1, the production of singlet oxygen by the boronated phthalocyanine described in Example 21 is similar to that of a not-substituted phthalocyanine. This leads to the conclusion that the presence of boronated substituents does not affect the photodynamic efficiency of the phthalocyanine in the products subject of the present invention.

Assessment of Photostability

Figure 2A:
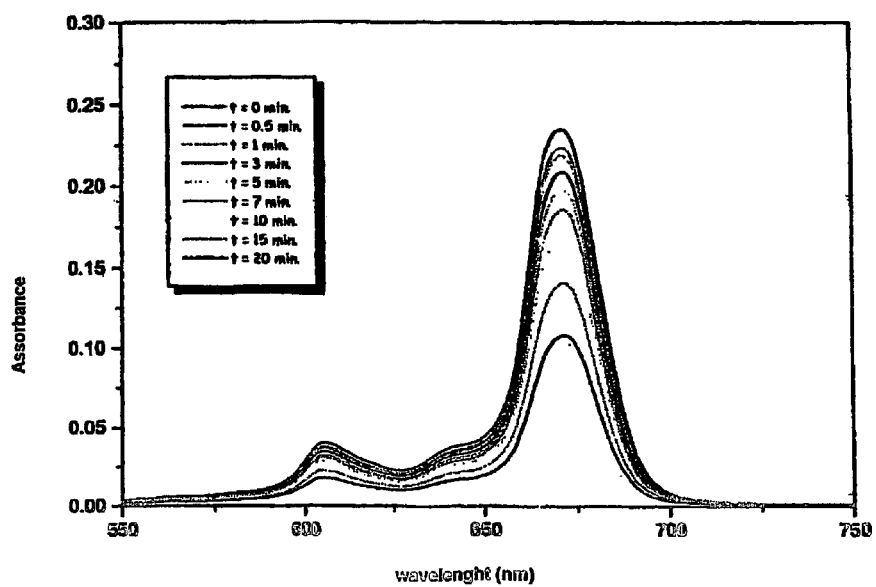
FIG. 2A: Absorption spectrum and determination of the degraded unsubstituted zinc phthalocyanine, irradiated according to the experimental conditions described above for FIG. 1.
Figure 2B:
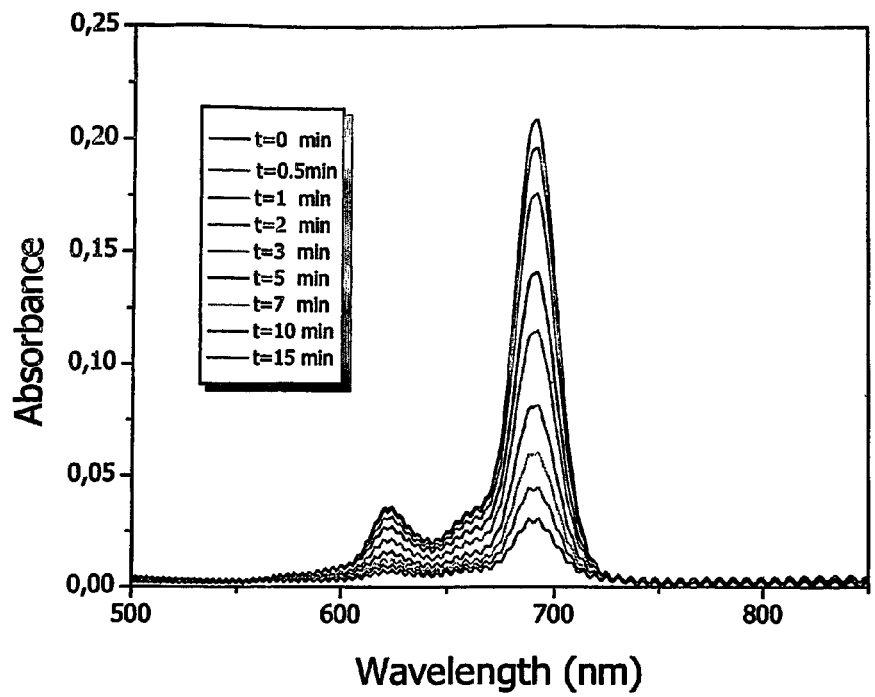
FIG. 2B: Absorption spectrum and determination of degraded boronated phthalocyanine, prepared according the Example 21, irradiated according to the experimental conditions described in FIG. 1.

It is known that most phthalocyanines are subjected to a more or less extensive photobleaching under visible light irradiation. It is therefore important to define if the rate constant of this process is too fast, so that the active principle is photodegraded at a high rate, which could negatively interfere with the photosensitization of cells or other substrates. The photostability of tetra-substituted boronated phthalocyanine, prepared as described in Example 21, has been performed spectrophotometrically and the results shown in FIG. 2B. Results obtained with a not substituted phthalocyanine are reported. In FIG. 2A as a reference. From comparison of the plots shown in FIGS. 2A and 2B it may be concluded that 1- the boron substituted molecules prepared according to the present invention are as useful photosensitizers able to absorb red visible light as the unsubstituted ones;

2- the photobleaching kinetics undergoes only limited changes when the phthalocyanine structure is modified by introduction of boronated groups. Indeed, the more extensive photobleaching found for the boronated compound has the advantage to induce an easier elimination of excess drug, thereby avoiding the onset of delayed photosensitization, obviously compared to its control represented by a not-boronated compound.

Assessment of Activity on Biological Substrates

Figure 3A:
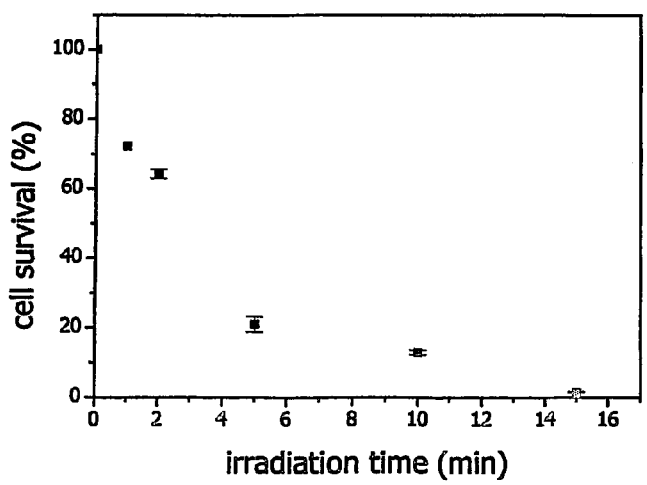
FIG. 3: Percentage survival of transformed B16F1 murine melanocites as a function of the irradiation time after 24 hours incubation with boronated phthalocyanine prepared according to Example 21, as a DL α-dipalmitoyl phosphatidylcoline (DPPC) liposomal preparation (3A) or a DOPC liposomal preparation (3B). Irradiations were performed as described above for FIG. 1.
Figure 3B:
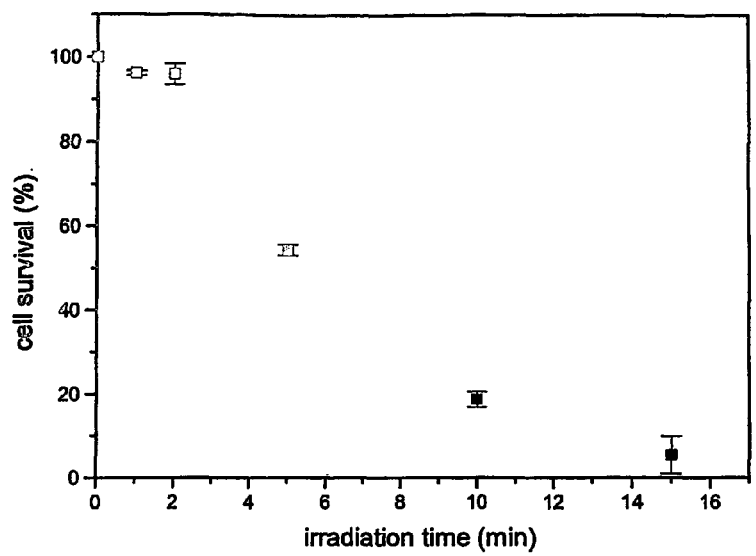

The tetra-substituted boronated phthalocyanine prepared as described in Example 21 has been used for the photosensitization of melanocytes deriving from murine pigmented melanoma B16-F1. Melanocytes were incubated (24 hrs) with a DPCC or DOPC liposomal phthalocyanine preparation (7 microM). After incubation, the cells were washed with PBS and irradiated with red visible light (600-750 nm, 50 mW/cm$^2$). Survival was determined after the photo-treatment (18-24 hrs) by the Trypan Blue exclusion test. Results for delivered phthalocyanine are summarised in FIG. 3A (DPPC liposomes) and in FIG. 3B (DOPC liposomes). It can be concluded that an almost complete cell mortality is achieved with irradiation times as low as 10 min.

Figure 4A:
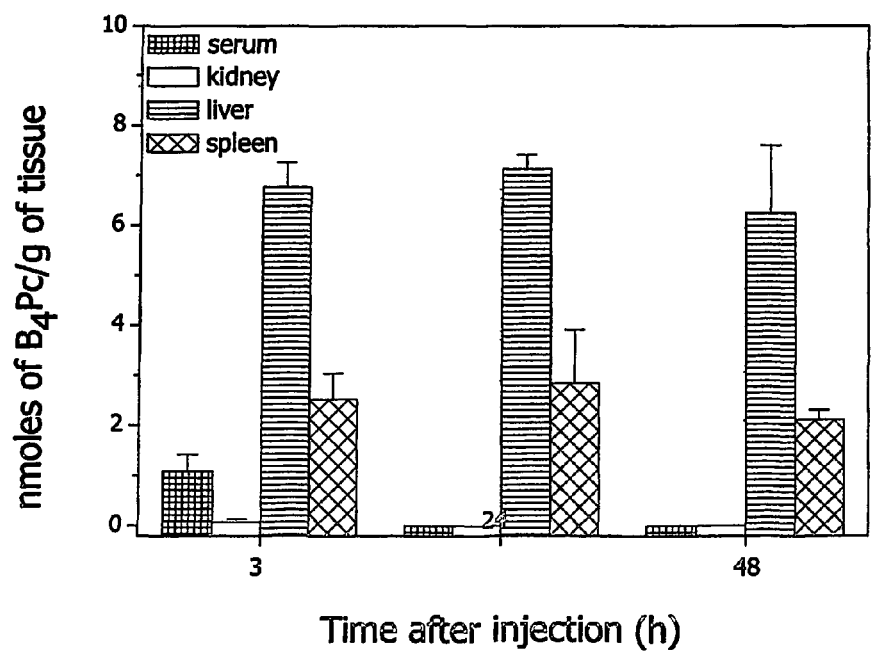
FIG. 4: Time-dependence of boronated phthalocyanine (B$_4$Pc) recovery from plasma and selected tissues of B16-F1 pigmented melanoma bearing C57/BL6 mice (4A) as well as from tumour and skin (4B), after intravenous administration of 0.75 mg/Kg of boronated phthalocyanine according to Example 21 as DPPC liposomal preparation.
Figure 4B:
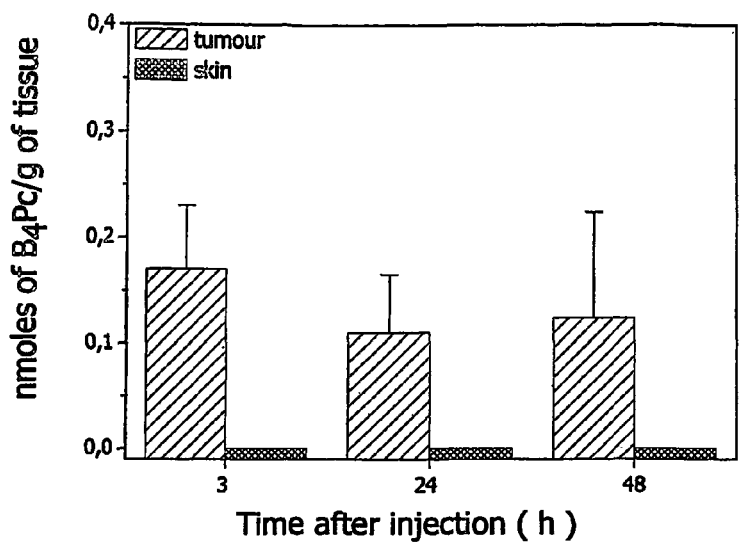
Figure 5A:
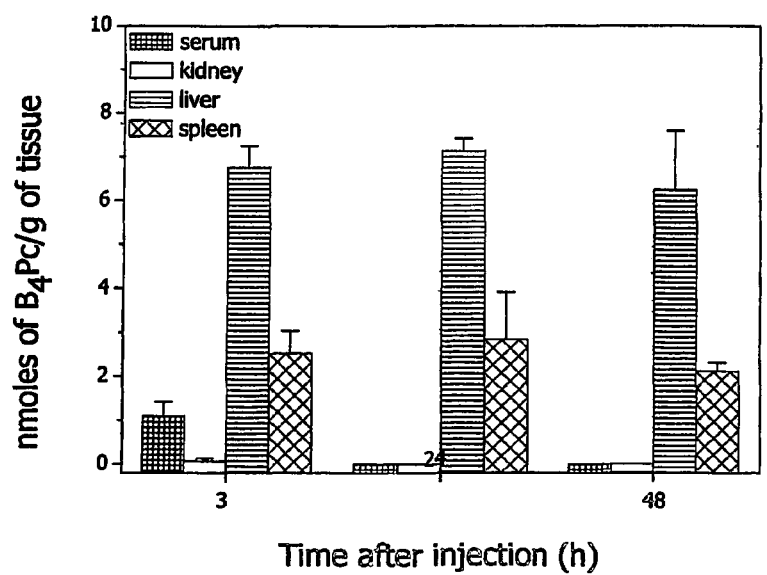
FIG. 5: Time-dependence of boronated phthalocyanine (B$_4$Pc) recovery from plasma and selected tissues of B16-F1 pigmented melanoma bearing C57/BL6 mice (5A), as well as from tumour and skin (5B) after iv administration of 3.0 mg/Kg of boronated phthalocyanine according to Example 21 as DOPC liposomal preparation.
Figure 5B:
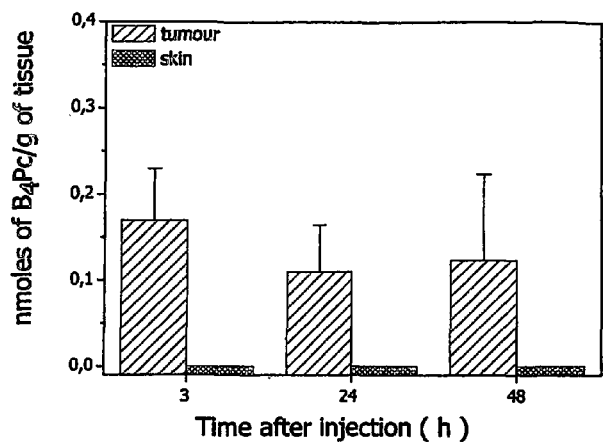

Through pharmacokinetic experiments on B16-F1 pigmented melanoma bearing mice, a number of studies such as tissue affinity, uptake kinetics on various organs, clearance from the body and selectivity for the tumour tissues have been evaluated, using the product described in Example 21. Toward this aim, once tumours had reached the volumes of 0.81 cm$^2$, the boronated phthalocyanine as DPPC liposomal preparation (0.75 mg/kg) or as a DOPC liposomal preparation (3 mg/kg) was systemically administered. Animals were sacrified (after 3, 24, 48 hrs) and the phthalocyanine concentration determined in plasma and selected tissues spectrophotometrically. The results are shown in FIG. 4 (DPPC liposomes) and in FIG. 5 (DOPC liposomes) and indicate that the clearance of this product from plasma is rapid with no product residue at 24 hrs after the treatment. The large recovery of phthalocyanine from the components of the reticuloendothelial system, such as liver and spleen, is to be expected for compounds which are delivered via liposomes.

Figure 6:
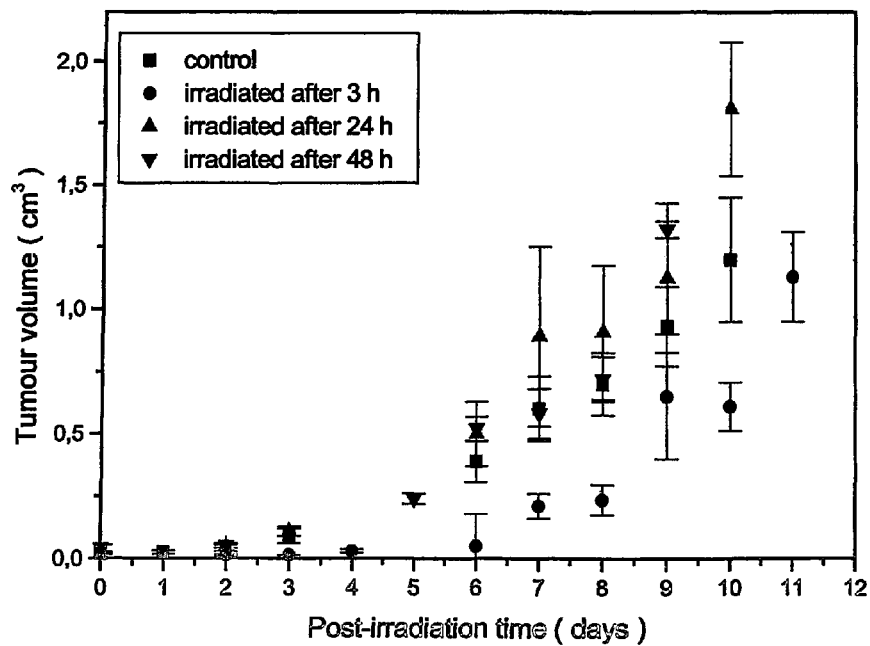
FIG. 6: Rate of tumour growth as a function of post-irradiation time in C57/BL6 mice bearing a B16F1 transplanted pigmented melanoma which have been intravenously injected with 6.0 mg/kg boronated phthalocyanine prepared according to Example 21 as a DOPC liposomal preparation and then irradiated by red visible light (670 nm from a diode laser) at a fluence-rate of 200 mW/cm$^2$ and a total light dose of 250 J/cm$^2$.
Figure 7:
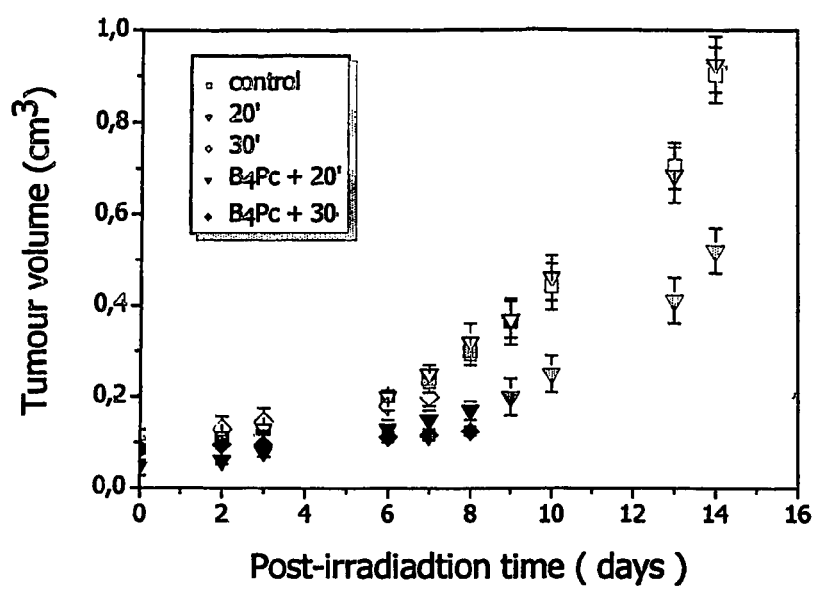
FIG. 7: Rate of tumour growth as a function of post-irradiation time in C57/BL6 mice bearing a B16F1 transplanted pigmented melanoma which have been intravenously injected with 6.0 mg/kg boronated phthalocyanine prepared according to Example 23, as a DOPC liposomal preparation, and at 24 hours from injection were irradiated by thermal neutrons for 20 and 30 min. The growth profile of the radiosensitized pigmented melanoma is compared with that obtained for untreated control mice.

Moreover, as one can see in FIG. 6, the boronated phthalocyanine is able to induce a significant delay in the rate of tumour growth, when the mice bearing a subcutaneously transplanted pigmented melanoma are exposed to red light. The tumour response is most evident if the irradiations are carried out at 3 h after injection of the photosensitizer.

A significant delay in tumour growth is also observed for the mice which are irradiated with thermal neutrons at 24 h, after intravenous injection of the boronated phthalocyanine reported in Example 23 incorporated in DOPC liposomes. This shows that the amount of phthalocyanine accumulated in the tumour under our experimental conditions is sufficient to achieve the BNCT effect. As a consequence, an extensive tumour necrosis is caused.

The boron substituted phthalocyanines of the present invention are able to localize in the melanoma at appreciable concentrations, in which a reduction of the tumour, as result of photoinactivation, was obtained.

The tetra-substituted phthalocyanine, reported in Example 21 is accumulated in large amounts, both in the liver and in the spleen, and, at least the phthalocyanine delivered via DOPC liposomes, is largely cleared from liver and spleen after 1 week from injection. This would indicate that no persistent general photosensitivity can be expected beyond one week after the administration of the phthalocyanine. Very limited amounts of phthalocyanine are recovered from the kidneys, which suggests that the photosensitizer is cleared from the organism almost exclusively via the bile-gut pathway.

The selectivity of tetra-substituted phthalocyanine (Example 21) localization in the tumour is, on the whole, acceptable, since small amounts of photosensitizer were found in the skin that, in this animal model, represents the peritumoural tissue. This circumstance clearly favours the application of either PDT or BNCT treatments, since an extensive damage of the tumour tissue can be achieved with minimal damage at the level of the surrounding healthy tissues, as shown by our experimental results.

The compounds of formula (I), reported in the present invention, are therefore useful for treatment of tumours, precancerous and hyperproliferative conditions, using a combined PDT/BNCT approach, further benefiting from their fluorescence emission properties, that allow the identification of the pathological areas before and during the therapeutic treatment.

The products can be administered parenterally, by using pharmaceutical formulations known in the state of the art, and proceeding with the BNCT/PDT treatment, after localization has taken place.

The invention claimed is:

1. A compound of general formula (I)

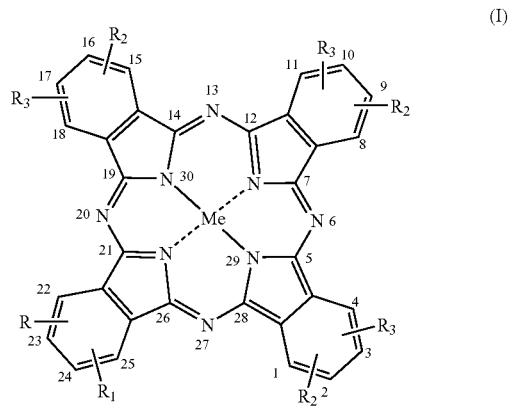

in which:
Me is selected from the group consisting of Zn, AlOR$_4$ and Si(OR$_4$), wherein R$_4$ is selected from the group consisting of H and C1-C15 alkyl,
R, R$_1$, R$_2$ and R$_3$, equal or different from one other, are selected from H and groups (G)$_s$-(X)$_t$-(Y-Z)$_u$ wherein:
G is selected from the group consisting of O, S, SO, CH$_2$ and N;
X is selected from the group consisting of phenyl, linear or branched C1-C10 alkyl, C1-C10 alkenyl and C1-C10 alkynyl;

Y is selected from the group consisting of S, $(CH_2)_n$, phenyl, $O-(CH_2)_n$, $(CH_2)_n-O-$, $(CH_2CH_2O)_n$, CONH, NHCO, COO, COS, and 3-mercapto-pyrrolidine-2,5-dione;

Z is selected from the group consisting of $^{11}$B-(o,m,p-carborane), $^{11}$B-undecahydrododecaboromercaptyl, $^{11}$B-undecahydrododecaborate, $^{10}$B-(o,m,p-carborane), $^{10}$B-undecahydrododecaboromercaptyl and $^{10}$B-undecahydrododecaborate;

n is an integer comprised between 1 and 10;
s is 0, 1;
t is 0, 1;
u is an integer comprised between 1 and 3;
with the proviso that at least one among R, $R_1$, $R_2$ and $R_3$ is different from H, and when only one amongst R, $R_1$, $R_2$ and $R_3$ is different from H, u is different from 1;
and pharmaceutically acceptable salts thereof.

2. The compound of general formula (I) according to claim 1, in which $R_1=R_2=H$ and R and $R_3$ are different from H and equal between each other.

3. The compound according to claim 1, wherein Me is Zn.

4. The compound according to claim 1, wherein G is O, X is phenyl and Y is $CH_2$.

5. The compound according to claim 1, selected from the following compounds:
- 1,8(11),15(18),22(25)-tetrakis-{[4-($^{11}$B-o-carboran-1-yl)methyl]phenoxy}-phthalo cyaninate zinc(II);
- 2,9(10),16(17),23(24)-tetrakis-{[4-($^{11}$B-o-carboran-1-yl)methyl]phenoxy}-phthalo cyaninate zinc(II);
- 1,8(11),15(18),22(25)-tetrakis-{[4-($^{10}$B-o-carboran-1-yl)methyl]phenoxy}-phthalo cyaninate zinc(II);
- 2,9(10),16(17),23(24)-tetrakis-{[3,5-bis-($^{11}$B-o-carboran-1-yl)methyl]phenoxy}-phthalocyaninate zinc(II);
- 1,8(11),15(18),22(25)-tetrakis-{[3,5-bis-($^{11}$B-o-carboran-1-yl)methyl]phenoxy}-phthalo cyaninate zinc(II);
- 1,8(11),15(18),22(25)-tetrakis-{[3,5-bis-($^{10}$B-o-carboran-1-yl)methyl]phenoxy}-phthalo cyaninate zinc(II);
- 2,9(10),16(17),23(24)-tetrakis-{[3,5-bis-($^{10}$B-o-carboran-1-yl)methyl]phenoxy}-phthalo cyaninate zinc(II);
- 2,3,9,10,16,17,23,24-octakis-{[4-($^{11}$B-o-carboran-1-yl)methyl]phenoxy}-phthalocyaninate zinc(II);
- 2,3,9,10,16,17,23,24-octakis-{[4-($^{10}$B-o-carboran-1-yl)methyl]phenoxy}-phthalocyaninate zinc(II);
- 2,9(10),16(17),23(24)-tetrakis-{[4-($^{10}$B-o-carboran-1-yl)methyl]phenoxy}-phthalocyaninate zinc(II);
- 2-{3,5-[bis-($^{11}$B-o-carboran-1-yl)methyl]phenoxy}-phthalocyaninate zinc(II);
- 2-{3,5-[bis-($^{10}$B-o-carboran-1-yl)methyl]phenoxy}-phthalocyaninate zinc(II);
- 1-{3,5-[bis-($^{11}$B-o-carboran-1-yl)methyl]phenoxy}-phthalocyaninate zinc(II);
- 1-{3,5-[bis-($^{10}$B-o-carboran-1-yl)methyl]phenoxy}-phthalocyaninate zinc(II);
- 2,3-bis-{[4-($^{11}$B-o-carboran-1-yl)methyl]phenoxy}-phthalocyaninate zinc(II);
- 2,3-bis-{[4-($^{10}$B-o-carboran-1-yl)methyl]phenoxy}-phthalocyaninate zinc(II);
- 2-{2,4,6-[tris($^{11}$B-o-carboran-1-yl)methyl]phenoxy}-phthalocyaninate zinc(II);
- 2-{2,4,6-[tris($^{10}$B-o-carboran-1-yl)methyl]phenoxy}-phthalocyaninate zinc(II);
- 1-{2,4,6-[tris($^{11}$B-o-carboran-1-yl)methyl]phenoxy}-phthalocyaninate zinc(II); and
- 1-{2,4,6-[tris($^{10}$B-o-carboran-1-yl)methyl]phenoxy}-phthalocyaninate zinc(II).

6. A pharmaceutical composition comprising a compound of claim 1 or mixtures thereof, and pharmaceutically acceptable excipients and/or diluents.

7. A diagnostic agent comprising a compound of claim 1, and a pharmaceutically acceptable carrier.

8. A method for the treatment of tissues affected by tumors, pre-cancerous conditions and pathological diseases characterized by cellular hyperproliferation by PhotoDynamic Therapy, comprising administering to a patient in need of such a treatment an effective amount of at least a compound of general formula (I) as defined in claim 1.

9. A method of treating tissues affected by tumors, pre-cancerous conditions and pathological diseases characterized by cellular hyperproliferation by Boron Neutron Capture Therapy, comprising administering to a patient in need of such a treatment an effective amount of at least a compound of general formula (I) as defined in claim 1.

10. A method of treating tissues affected by tumors, pre-cancerous conditions and pathological diseases characterized by cellular hyperproliferation by sequential application of PhotoDynamic Therapy and Boron Neutron Capture Therapy, comprising administering to a patient in need of such a treatment an effective amount of at least a compound of general formula (I) as defined in claim 1.

* * * * *